United States Patent [19]

Grieve et al.

[11] Patent Number: 5,766,609
[45] Date of Patent: Jun. 16, 1998

[54] USE OF PROTEASE INHIBITORS AND PROTEASE VACCINES TO PROTECT ANIMALS FROM FLEA INFESTATION

[75] Inventors: Robert B. Grieve, Windsor; Keith E. Rushlow; Shirley Wu Hunter, both of Ft. Collins; Glenn R. Frank, Wellington, all of Colo.; Andrew Heath, Sheffield, United Kingdom; Miles Yamanaka, Sacramento, Calif.; Ann Arfsten, Belmont, Calif.; Beverly Dale, Los Altos, Calif.

[73] Assignee: Heska Corporation, Ft. Collins, Colo.

[21] Appl. No.: 326,773

[22] Filed: Oct. 18, 1994

Related U.S. Application Data

[63] Continuation-in-part of Ser. No. 806,482, Dec. 13, 1991, Pat. No. 5,356,622.

[51] Int. Cl.$^6$ .............................. A61K 39/00; C07K 1/00
[52] U.S. Cl. ...................... 424/265.1; 530/350; 530/858
[58] Field of Search ........................ 424/265.1; 530/350, 530/58

[56] References Cited

U.S. PATENT DOCUMENTS 5,356,622  10/1994  Heath et al. ........................ 424/265.1

FOREIGN PATENT DOCUMENTS

WO 90/03433  4/1990  WIPO .

OTHER PUBLICATIONS

Lehane et al Int. J. Parasitology 24(1): 27–32, 1994.
Eldridge et al Semin Hemotal 30 (4 Suppl 4): 16–25, 1993.
Houk et al., pp. 135–146, 1986, Archives of Insect Biochemistry and Physiology, vol. 3.
Young et al., 1963, Exp. Parasitol., 13:155–166.
Azad et al., Am. J. Trop. Med. Hyg., 1987, 37:629–635.
Billingsley, Annu. Rev. Entomol., 1990, 35:219–248.
Borovsky et al., FASEB J., 1990, 4:3015–3020.
Borovsky, Arch. Insect Biochem. Physiol., 1988, 7:187–210.
Casu et al., Insect Mol. Biol., 1994, 3(4):201–211.
Casu et al., Insect. Mol. Biol., 1994, 3(3):159–170.
Cherney et al., Am J. Trop. Med., 1939, 19:327–332.
Chinzel et al., Med. Vet. Entomol., 1987, 1:409–416.
Elvin et al., Mol. Gen. Genet., 1993, 240:132–139.
Halliwell, J. Immunol., 1973, 110:422–430.
Halliwell et al., J. Allerg. Clin. Immunol., 1978, 62:236–242.
Halliwell et al., Vet. Immunol. Immunopathol., 1985, 8:215–223.
Hatfield, Med. Vet. Entomol., 1988, 2:331–338.
Hatfield, Med. Vet. Entomol., 1988, 2:339–345.
Johnston et al., Int. J. Parasitol., 1986, 16(1):27–34.
Kalhok et al., Insect Mol. Biol., 1993, 2(2):71–79.
Kay et al., Am. J. Trop. Med. Hyg., 1994, 50(6) Suppl.:87–96.
Kemp et al., Internat. J. Parasitol., 1986, 16, 115–120.
Kwochka, Vet. Clin. North Am., 1987, 17:1235–1262.
Law et al., Annu. Rev. Biochem., 1992, 61:87–111.
McFarlane, "Nutrition and Digestive Organs", in Fundamentals of Insect Physiology, M.S. Blum, ed., John Wiley and Sons, New York, New York, 1985, pp. 59–89.
Müller et al., EMBO J., 1993, 12(7):2891–2900.
Nesbitt et al., J. Am. Vet. Med. Assoc., 1978, 173:282–288.
Opdebeeck et al., Immunol., 1988, 63:363–367.
Opdebeeck et al., Parasite Immunol., 1988, 10:405–410.
Opdebeeck et al., Immunol., 1989, 67:388.
Otieno et al., Insect Sci. Applic., 1984, 5(4):297–302.
Ramos et al., Insect Mol. Biol., 1993, 1(3):149–163.
Rand et al., Proc. Natl. Acad. Sci. (USA), 1989, 86:9657–9661.
Ribiero, Ann. Rev. Entomol., 1987, 32:463–478.
Sandeman et al., Int. J. Parasitol., 1990, 20(8):1019–1023.
Schlein et al., Physiol. Entomol., 1976, 1:55–59.
Soulsby, in Helminths, Arthropods and Protozoa of Domesticated Animals, 7th ed., 1982, Lea and Febiger, eds., Philadelphia, PA, pp. 378–384.
Vaughn et al., J. Med. Entomol., 1988, 25:472–474.
Wikel, Vet. Parasitol., 1984, 14:321–329.
Wikel, Vet. Parasitol., 1988, 29:235–264.
Willadsen et al., J. Immunol., 1989, 143:1346–1351.
Wong et al., Immunol., 1989, 66, 149–155.
Jany et al., 1983, Biochem. & Biophys. Res. Comm., 110(1):1–7.
Sarkar et al., 1990, Genomics, 61(1):133–143.
Cuypers et al., 1982, J. Biol. Chem., 257(12):7077–7085.
Matsushima et al., 1991, Biochem. Biophys. Res. Comm., 178(3):1459–1464.

Primary Examiner—James C. Housel
Assistant Examiner—Rodney P. Swartz
Attorney, Agent, or Firm—Sheridan Ross P.C.

[57] ABSTRACT

A method to protect a host animal from flea infestation by treating that animal with a composition that includes a compound that reduces protease activity of fleas feeding from the treated animal, thereby reducing flea burden on the animal and in the environment of the animal. The present invention also relates to compositions including flea protease vaccines, anti-flea protease antibodies and/or protease inhibitors. Also included in the present invention are soluble flea midgut preparations, flea protease proteins, nucleic acid molecules encoding such proteins and antibodies that selectively bind to such proteins. The present invention also includes methods to obtain and use such preparations, proteins, nucleic acid molecules, antibodies and protease inhibitors to protect an animal from flea infestation.

23 Claims, 9 Drawing Sheets

USE OF PROTEASE INHIBITORS AND PROTEASE VACCINES TO PROTECT ANIMALS FROM FLEA INFESTATION

CROSS-REFERENCE TO RELATED APPLICATIONS

The present application is a continuation-in-part of U.S. patent application Ser. No. 07/806,482, entitled "Flea Midgut-Generated Antiflea Vaccines", filed Dec. 13, 1991, now U.S. Pat. No. 5,356,662, and which is incorporated by reference herein in its entirety.

FIELD OF THE INVENTION

The present invention relates to novel flea protease proteins and their use to reduce flea infestation of animals. The present invention also relates to the use of anti-flea protease antibodies and other compounds that reduce flea protease activity to reduce flea infestation of animals.

BACKGROUND OF THE INVENTION

Fleas, which belong to the insect order Siphonaptera, are obligate ectoparasites for a wide variety of animals, including birds and mammals. Flea infestation of animals is of health and economic concern because fleas are known to cause and/or transmit a variety of diseases. Fleas cause and/or carry infectious agents that cause, for example, flea allergy dermatitis, anemia, murine typhus, plague and tapeworm. In addition, fleas are a problem for animals maintained as pets because the infestation becomes a source of annoyance for the pet owner who may find his or her home generally contaminated with fleas which feed on the pets. As such, fleas are a problem not only when they are on an animal but also when they are in the general environment of the animal.

The medical and veterinary importance of flea infestation has prompted the development of reagents capable of controlling flea infestation. Commonly encountered methods to control flea infestation are generally focussed on use of insecticides in formulations such as sprays, shampoos, dusts, dips, or foams, or in pet collars. While some of these products are efficacious, most, at best, offer protection of a very limited duration. Furthermore, many of the methods are often not successful in reducing flea populations on the pet for one or more of the following reasons: (1) failure of owner compliance (frequent administration is required); (2) behavioral or physiological intolerance of the pet to the pesticide product or means of administration; and (3) the emergence of flea populations resistant to the prescribed dose of pesticide. Additional anti-flea products include non-toxic reagents such as insect growth regulators (IGRs), including methoprene, which mimics flea hormones and affect flea larval development.

An alternative method for controlling flea infestation is the use of flea vaccines to be administered to animals prior to or during flea infestation. However, despite considerable interest in developing anti-flea reagents, no flea vaccine presently exists.

SUMMARY OF THE INVENTION

The present invention relates to a method to protect a host animal from flea infestation that includes the step of treating that animal with a composition that includes a compound that reduces protease activity of fleas feeding from the treated animal, thereby reducing flea burden on the animal and in the environment of the animal. Flea proteases to target can be aminopeptidases, carboxypeptidases and/or endopeptidases, and can include serine proteases, metalloproteases, aspartic acid proteases and cysteine proteases.

Preferred compounds to include in a composition of the present invention include one or more of the following: flea protease vaccines, anti-flea protease antibodies and/or protease inhibitors. Also included in the present invention are compositions including such compounds. Particularly preferred compounds are those that reduce the activity of flea serine proteases, with flea serine protease vaccines being even more preferred.

Another embodiment of the present invention is a controlled release formulation that includes one or more compositions of the present invention and use of such a formulation to provide long term protection against flea infestation.

In a preferred embodiment, treatment of an animal with a composition of the present invention reduces flea viability by at least about 50 percent within at least about 21 days after fleas begin feeding from a treated animal. In another embodiment, treating an animal with a composition of the present invention reduces flea fecundity by at least about 50 percent within at least about 30 days after fleas begin feeding from a treated animal.

The present invention also includes a method to protect a host animal from flea infestation, which includes treating the animal with a composition comprising a first compound capable of reducing flea protease activity and a second compound that reduces flea burden by a method other than by reducing flea protease activity. In this embodiment, the first compound, by reducing proteolytic activity in the flea midgut, can enhance the efficacy of a second compound that also enters the flea through its midgut and otherwise would be susceptible to proteolytic degradation. Also included in the present invention are compositions including such first and second compounds.

Also included in the present invention is a method to reduce flea infestation that includes treating a flea directly or an animal susceptible to flea infestation with a composition comprising a compound capable of reducing flea protease activity.

Another aspect of the present invention is a soluble flea midgut preparation having proteolytic activity, wherein at least about 70 percent of that proteolytic activity can be inhibited by 4-2-aminoethyl-benzenesulfonylfluoride-hydrochloride (i.e., wherein about 70 percent of that activity is serine protease activity). Such a preparation is preferably produced by (a) disrupting a flea midgut to produce a mixture comprising a liquid portion and a solid portion; and (b) recovering the liquid portion to obtain the preparation. A flea protease can be obtained from such a preparation using any of a variety of purification techniques.

The present invention also includes an isolated protein that includes an amino acid sequence encoded by a nucleic acid molecule capable of hybridizing under stringent conditions with a nucleic acid molecule that encodes a midgut protease present in a flea midgut. Such a protein preferably has proteolytic activity and/or the ability to elicit an immune response against a flea midgut protease. Also included in the present invention is an isolated flea protease protein that includes an amino acid sequence encoded by a nucleic acid molecule capable of hybridizing under stringent conditions with a nucleic acid molecule that encodes a flea midgut protease having an amino acid sequence including SEQ ID NO:1.

The present invention also includes a nucleic acid molecule capable of hybridizing under stringent conditions with a gene encoding a flea protease present in a flea midgut. Also included are recombinant molecules including one or more nucleic acid molecules of the present invention as well as recombinant cells including one or more nucleic acid molecules of the present invention. Nucleic acid molecules encoding flea protease proteins of the present invention can be used in the production of such proteins.

The present invention also includes isolated antibodies capable of selectively binding to a protease present in a flea midgut. Such antibodies have a variety of uses including in passive immunization protocols.

Another aspect of the present invention is a method to identify a compound capable of inhibiting the proteolytic activity of a flea protease. Such a method includes the steps of (a) contacting an isolated flea protease protein with a putative inhibitory compound under conditions in which, in the absence of the compound, the protease has proteolytic activity; and (b) determining if the putative inhibitory compound inhibits the activity of the protease. Also included in the present invention is a test kit to identify a compound capable of inhibiting proteolytic activity of a flea protease. Such a kit includes an isolated flea protease protein having proteolytic activity and a means for determining the extent of inhibition of that activity in the presence of a putative inhibitory compound.

DETAILED DESCRIPTION OF THE INVENTION

Figure 1:
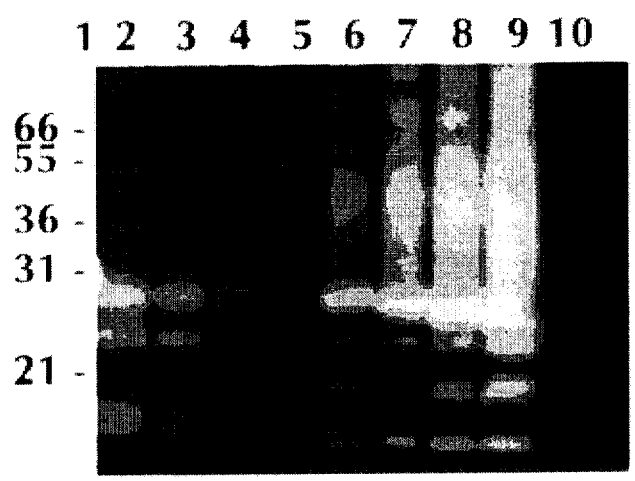
FIG. 1 depicts a protease substrate gel analysis of the relative proteolytic activity in 1, 2, 5 or 10 midguts from either fed or unfed female fleas.

The present invention includes the use of compounds that inhibit flea protease activity to protect a host animal from flea infestation. The inventors have discovered that proteases are significant components of the flea midgut and are good targets for immunotherapeutic and/or chemotherapeutic intervention to reduce flea burden both on the host animal and in the immediate (i.e., surrounding) environment of the animal. The inventors have shown, for example, that the viability and/or fecundity of fleas consuming a blood meal is reduced when the blood meal contains compounds that reduce flea protease activity, probably because the compounds interfere with flea digestion and other functions. Compounds that reduce the amount and/or activity of flea proteases without substantially harming the host animal are included in the present invention. Such compounds include flea protease vaccines, anti-flea protease antibodies, flea protease inhibitors, and/or compounds that suppress protease synthesis; such compounds are discussed in more detail below.

One embodiment of the present invention is a method to protect a host animal from flea infestation by treating the animal with a composition that includes a compound that reduces the protease activity of fleas feeding (includes fleas in the process of feeding as well as fleas having fed) from the treated animal thereby reducing the flea burden on the animal and in the environment of the animal. It is to be noted that the term "a" or "an" entity refers to one or more of that entity; for example, a compound refers to one or more compounds. As such, the terms "a" (or "an"), "one or more" and "at least one" can be used interchangeably herein. Thus, a composition of the present invention can include one or more compounds that target (reduced the activity of) one or more proteases in the flea.

As used herein, the phrase "to protect an animal from flea infestation" refers to reducing the potential for flea population expansion on and around the animal (i.e., reducing the flea burden). Preferably, the flea population size is decreased, optimally to an extent that the animal is no longer bothered by fleas. A host animal, as used herein, is an animal from which fleas can feed by attaching to and feeding through the skin of the animal. Fleas, and other ectoparasites, can live on a host animal for an extended period of time or can attach temporarily to an animal in order to feed. At any given time, a certain percentage of a flea population can be on a host animal whereas the remainder can be in the environment surrounding the animal (i.e., in the environment of the animal). Such an environment can include not only adult fleas, but also flea eggs and/or flea larvae. The environment can be of any size such that fleas in the environment are able to jump onto and off of a host animal. As such, it is desirable not only to reduce the flea burden on an animal per se, but also to reduce the flea burden in the environment surrounding the animal.

In accordance with the present invention, a host animal is treated by administering to the animal a compound of the present invention in such a manner that the compound itself (e.g., a protease inhibitor, protease synthesis suppressor or anti-flea protease antibody) or a product generated by the animal in response to administration of the compound (e.g., antibodies produced in response to a flea protease vaccine, or conversion of an inactive inhibitor "prodrug" to an active protease inhibitor) ultimately enters the flea midgut. An animal is preferably treated in such a way that the compound or product thereof enters the blood stream of the animal. Fleas are then exposed to the compound when they feed from the animal. For example, flea protease inhibitors administered to an animal are administered in such a way that the inhibitors enter the blood stream of the animal, where they can be taken up by feeding fleas. In another embodiment, when a host animal is administered a flea protease vaccine, the treated animal mounts an immune response resulting in the production of antibodies against the protease (anti-flea protease antibodies) which circulate in the animal's blood stream and are taken up by fleas upon feeding. Blood taken up by fleas enters the flea midgut where compounds of the present invention, or products thereof, such as anti-flea protease antibodies, flea protease inhibitors, and/or protease synthesis suppressors, interact with, and reduce proteolytic activity in the flea midgut.

In accordance with the present invention, reducing proteolytic activity in flea midguts can lead to a number of outcomes that reduce flea burden on treated animals and their surrounding environments. Such outcomes include, but are not limited to, (a) reducing the viability of fleas that feed from the treated animal, (b) reducing the fecundity of female fleas that feed from the treated animal, (c) reducing the reproductive capacity of male fleas that feed from the treated animal, (d) reducing the viability of eggs laid by female fleas that feed from the treated animal, (e) altering the blood feeding behavior of fleas that feed from the treated animal (e.g., fleas take up less volume per feeding or feed less frequently), (f) reducing the viability of flea larvae, for example due to the feeding of larvae from feces of fleas that feed from the treated animal and/or (g) altering the development of flea larvae (e.g., by decreasing feeding behavior, inhibiting growth, inhibiting (e.g., slowing or blocking) molting, and/or otherwise inhibiting maturation to adults).

One embodiment of the present invention is a composition that includes one or more compounds that reduce the activity of one or more flea proteases directly (e.g., an anti-flea protease antibody or a flea protease inhibitor) and/or indirectly (e.g., a flea protease vaccine). Suitable flea proteases to target include flea aminopeptidases, flea carboxypeptidases and/or flea endopeptidases. Preferred flea proteases to target include, but are not limited to, serine proteases, metalloproteases, aspartic acid proteases and/or cysteine proteases. It is to be noted that these preferred groups of proteases include aminopeptidases, carboxypeptidases and/or endopeptidases. Preferred flea proteases to target include, but are not limited to, proteases that degrade hemoglobin, proteases involved in blood coagulation and/or lytic (anti-coagulation) pathways, proteases involved in the maturation of peptide hormones, proteases that inhibit complement or other host immune response elements (e.g., antibodies) and/or proteases involved in vitellogenesis. A number of proteases are known to those skilled in the art, including, but not limited to, aminopeptidases, such as leucine aminopeptidase and aminopeptidases B and M; astacin-like metalloproteases; calpains; carboxypeptidases, such as carboxypeptidases A, P and Y; cathepsins, such as cathepsins B, D, E, G, H, and L, chymotrypsins; cruzipains; meprins; papains; pepsins; renins; thermolysins and trypsins. A particularly preferred protease to target is a protease having a proteolytic activity that, when targeted with a composition of the present invention, reduces flea burden without substantially harming the host animal. Such a protease can be identified using, for example, methods as disclosed herein.

One aspect of the present invention is the discovery that a substantial amount of the proteolytic activity found in flea midguts is serine protease activity. Both in vitro and in vivo studies using a number of protease inhibitors substantiate this discovery, details of which are disclosed in the Examples. As such a particularly preferred protease to target is a serine protease. Examples of serine proteases, include, but are not limited to, acrosins, bromelains, cathepsin G, chymotrypsins, collagenases, elastases, factor Xa, ficins, kallikreins, papains, plasmins, Staphylococcal V8 proteases, thrombins and trypsins. In one embodiment, a preferred flea serine protease to target includes a protease having trypsin-like or chymotrypsin-like activity. It is appreciated by those skilled in the art that an enzyme having "like" proteolytic activity has similar activity to the referenced protease, although the exact structure of the preferred substrate cleaved may differ. "Like" proteases usually have similar tertiary structures as their referenced counterparts.

Protease inhibitor studies disclosed in the Examples section also indicate that additional preferred proteases to target include aminopeptidases and/or metalloproteases. Examples of such proteases include exo- and endo-metalloproteases, digestive enzymes, and enzymes involved in peptide hormone maturation. One example of an aminopeptidase that is also a metalloprotease is leucine aminopeptidase.

Suitable compounds to include in compositions of the present invention include, but are not limited to, a vaccine comprising a flea protease (a flea protease vaccine), an antibody that selectively binds to a flea protease (an anti-flea protease antibody), a flea protease inhibitor (a compound other than a vaccine or an antibody that inhibits a flea protease), and a mixture of such compounds. As used herein, a mixture thereof refers to a combination of one or more of the cited entities. Compositions of the present invention can also include compounds to suppress protease synthesis or maturation, such as, but not limited to, protease modulating peptides.

A preferred embodiment of the present invention is a flea protease vaccine and its use to reduce the flea population on and around an animal. A flea protease vaccine can include one or more proteins capable of eliciting an immune response against a flea protease and can also include other components. Preferred flea protease vaccines include a flea serine protease, a flea metalloprotease, a flea aspartic acid protease and/or a flea cysteine protease, with flea serine protease, flea metalloprotease and/or flea aminopeptidase vaccines being more preferred. Examples of flea protease vaccines include soluble flea midgut preparations of the present invention as well as one or more isolated proteins of the present invention.

One embodiment of the present invention is a soluble flea midgut preparation. Such a preparation includes primarily components naturally present in the lumen of a flea midgut and, depending on the method of preparation, can also include one or more peripheral midgut membrane proteins. Methods to preferentially include, or exclude, membrane proteins from such a preparation are known to those skilled in the art. The present invention includes the discovery that such a preparation has proteolytic activity, of which a substantial portion is serine protease activity. Preferably at least about 70 percent of the proteolytic activity in a soluble flea midgut soluble preparation is serine protease activity, as can be indicated by the ability to inhibit at least about 70 percent of the proteolytic activity with 4-2-aminoethyl-benzenesulfonylfluoride-hydrochloride (AEBSF). Serine protease activity can also be identified using other known inhibitors or substrates. Other preferred inhibitors that can inhibit at least about 70 percent of the proteolytic activity of a soluble flea midgut preparation of the present invention include soybean trypsin inhibitor, 1,3-diisopropylfluorophosphate or leupeptin.

A soluble flea midgut preparation of the present invention includes proteases that range in molecular weight from about 5 kilodaltons (kD) to about 200 kD, as determined by SDS-PAGE (sodium dodecyl sulfate polyacrylamide gel electrophoresis), with at least a substantial portion of the serine proteases ranging in molecular weight from about 5 kD to about 60 kD, as determined by SDS-PAGE. A substantial portion of protease activity in a soluble flea midgut preparation of the present invention has a pH activity optimum ranging from about pH 5 to about pH 10, preferably an activity optimum ranging from about pH 7 to about pH 9, and even more preferably an activity optimum of about pH 8. While not being bound by theory, such a pH optimum suggests that a large proportion of proteases in soluble flea midgut preparations of the present invention are serine proteases. It is also interesting to note that the pH of the flea midgut is also about pH 8. The findings that proteases in soluble flea midgut preparations of the present invention exhibit a varied pattern of inhibition by protease inhibitors of a given type (e.g., serine protease inhibitors), as well as variances seen in molecular weights and pH optima of the proteases, suggest that there are a number of protease isoforms in such preparations.

A soluble flea midgut preparation of the present invention is preferably prepared by a method that includes the steps of (a) disrupting a flea midgut to produce a mixture including a liquid portion and a solid portion and (b) recovering the liquid portion to obtain a soluble flea midgut preparation. Such a method is a simplified version of methods disclosed in Ser. No. 07/806,482, ibid. It is to be noted that in accordance with the present invention, methods disclosed in Ser. No. 07/806,482 ibid. can also be used to prepare soluble flea midgut preparations having similar proteolytic activities.

Flea midguts can be obtained (e.g., dissected from) from unfed fleas or from fleas that recently consumed a blood meal (i.e., blood-fed fleas). Such midguts are referred to herein as, respectively, unfed flea midguts and fed flea midguts. Flea midguts can be obtained from either male or female fleas. As demonstrated in the Examples section, female flea midguts exhibit somewhat more proteolytic activity than do male flea midguts. Furthermore, fed flea midguts have significantly more proteolytic activity than do unfed flea midguts. While not being bound by theory, it is believed that blood feeding induces in flea midguts the synthesis and/or activation of proteases as well as other factors (e.g., enzymes, other proteins, co-factors, etc.) important in digesting the blood meal, as well as in neutralizing host molecules potentially damaging to the flea (e.g., complement, immunoglobulins, blood coagulation factors). It is also to be appreciated that unfed flea midguts may contain significant targets not found in fed flea midguts and vice versa. Furthermore, although the present application focusses primarily on flea midgut proteases, it is to be noted that the present invention also includes other components of soluble flea midgut preparations of the present invention that provide suitable targets to reduce flea burden on an animal and in the environment of that animal; see also Ser. No. 07/806,482, ibid.

Methods to disrupt flea midguts in order to obtain a soluble flea midgut preparation are known to those skilled in the art and can be selected according to, for example, the volume being processed and the buffers being used. Such methods include any technique that promotes cell lysis, such as, but are not limited to, chemical disruption techniques (e.g., exposure of midguts to a detergent) as well as mechanical disruption techniques (e.g., homogenization, sonication, use of a tissue blender or glass beads, and freeze/thaw techniques).

Methods to recover a soluble flea midgut preparation are also known to those skilled in the art and can include any method by which the liquid portion of disrupted flea midguts is separated from the solid portion (e.g., filtration or centrifugation). In a preferred embodiment, disrupted flea midguts are submitted to centrifugation, preferably at an acceleration ranging from about 10,000×g to about 15,000×g for several minutes (e.g., from about 1 minute to about 15 minutes). The supernatant from such a centrifugation comprises a soluble flea midgut preparation of the present invention.

The present invention also includes an isolated protein that includes an amino acid sequence encoded by a nucleic acid molecule capable of hybridizing under stringent conditions with a nucleic acid molecule that encodes a protease present in (i.e., can be found in) a flea midgut, such as a midgut from a blood-fed female flea, a midgut from a blood-fed male flea, a midgut from an unfed female flea or a midgut from an unfed male flea. A preferred midgut protease is present in the lumen of the midgut.

An isolated protein of the present invention, also referred to herein as an isolated protease protein, preferably is capable of eliciting an immune response against a flea midgut protease and/or has proteolytic activity. According to the present invention, an isolated, or biologically pure, protein, is a protein that has been removed from its natural milieu. As such, "isolated" and "biologically pure" do not necessarily reflect the extent to which the protein has been purified. An isolated protease protein can be obtained from its natural source. Such an isolated protein can also be produced using recombinant DNA technology or chemical synthesis.

As used herein, an isolated protein of the present invention can be a full-length protein or any homologue of such a protein, such as a protein in which amino acids have been deleted (e.g., a truncated version of the protein, such as a peptide), inserted, inverted, substituted and/or derivatized (e.g., by glycosylation, phosphorylation, acetylation, myristylation, prenylation, palmitation, amidation and/or addition of glycosylphosphatidyl inositol) such that the homologue comprises a protein having an amino acid sequence that is sufficiently similar to a natural flea midgut protease that a nucleic acid sequence encoding the homologue is capable of hybridizing under stringent conditions to (i.e., with) a nucleic acid sequence encoding the corresponding natural flea midgut protease amino acid sequence. As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a protease protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a protease protein homologue of the present invention is from about 4 to about 6 amino acids in length, with preferred sizes depending on whether a full-length, multivalent (i.e., fusion protein having more than one domain each of which has a function), or functional portions of such proteins are desired. Protease protein homologues of the present invention preferably have protease activity and/or are capable of eliciting an immune response against a flea midgut protease.

A protease protein homologue of the present invention can be the result of allelic variation of a natural gene encoding a flea protease. A natural gene refers to the form of the gene found most often in nature. Protease protein homologues can be produced using techniques known in the art including, but not limited to, direct modifications to a gene encoding a protein using, for example, classic or recombinant DNA techniques to effect random or targeted mutagenesis. Isolated protease proteins of the present invention, including homologues, can be identified in a straightforward manner by the proteins' ability to effect proteolytic activity and/or to elicit an immune response against a flea midgut protease. Such techniques are known to those skilled in the art.

A preferred protease protein of the present invention is a flea serine protease, a flea metalloprotease, a flea aspartic acid protease, a flea cysteine protease, or a homologue of any of these proteases. A more preferred protease protein is a flea serine protease, a flea metalloprotease or a homologue of either. Also preferred is a flea aminopeptidase or a homologue thereof. Particularly preferred is a flea serine protease or a homologue thereof.

Preferred protease proteins of the present invention are flea protease proteins having molecular weights ranging from about 5 kD to about 200 kD, as determined by SDS-PAGE, and homologues of such proteins. More preferred are flea protease proteins having molecular weights ranging from about 5 kD to about 60 kD, as determined by SDS-PAGE, and homologues of such proteins. Even more preferred are flea serine protease proteins and particularly those having molecular weights of about 26 kD (denoted PfSP26), about 24 kD (denoted PfSP24), about 19 kD (denoted PfSP19) and about 6 kD (denoted PfSP6), as determined by SDS-PAGE, and homologues of such proteins.

A particularly preferred isolated protein of the present invention is a flea serine protease protein having a molecular weight of about 26 kD, denoted PfSP26, or a homologue of this protein. A partial amino (N-)-terminal amino acid sequence of PfSP26 protein has been determined to be Ile Ile Gly Glu Gly Val Ala Gly Glu Gly Ser Ala Pro Tyr Gln Val Ser Leu Arg Thr Lys Glu Gly Asn His Phe Ser Gly Gly Ser Ile Leu, denoted SEQ ID NO:1. It should be noted that since amino acid sequencing technology is not entirely error-free, SEQ ID NO:1 represents, at best, an apparent partial N-terminal amino acid sequence of PfSP26. Assuming the accuracy of SEQ ID NO:1, PfSP26, and homologues thereof, can also be referred to as proteins comprising an amino acid sequence encoded by a nucleic acid molecule capable of hybridizing under stringent conditions with a nucleic acid molecule that encodes a midgut protease that includes the amino acid sequence of SEQ ID NO:1, or at least a portion thereof. One embodiment of the present invention is a protein that has an amino acid sequence including at least a portion of SEQ ID NO:1. As used herein, a portion of SEQ ID NO:1 is an amino acid sequence that is at least sufficiently long to distinguish the protease as being a member of the PfSP26 protein family. A minimum length depends on the amount of homology, and is usually from about 5 to about 10 amino acids long.

One embodiment of the present invention is an isolated protein having proteolytic activity that is substantially inhibited by a serine protease inhibitor. Such inhibition can be measured by techniques known to those skilled in the art. To be substantially inhibited means that at least half of the proteolytic activity of the protease protein is inhibited by a serine protease inhibitor. Preferably at least about 70 percent, and even more preferably at least about 90 percent of the proteolytic activity of the protease protein is inhibited by a serine protease inhibitor.

An isolated protein of the present invention can be produced in a variety of ways, including recovering such a protein from a flea midgut and producing such a protein recombinantly. In one embodiment, a flea midgut protease can be recovered by methods heretofore disclosed for obtaining a soluble flea midgut preparation. A flea midgut protease protein can be further purified from a disrupted flea midgut by a number of techniques known to those skilled in the art, including, but not limited to, affinity chromatography, ion exchange chromatography, filtration, electrophoresis (e.g., standard, capillary and flow-through electrophoresis), hydrophobic interaction chromatography, gel filtration chromatography, reverse phase chromatography, concanavalin A chromatography, chromatofocusing and differential solubilization. In one embodiment, a flea midgut protease is purified using protease inhibitor affinity chromatography, an example of which is disclosed in the Examples section.

Another embodiment of the present invention is a method to produce an isolated protein of the present invention using recombinant DNA technology. Such a method includes the steps of (a) culturing a recombinant cell comprising a nucleic acid molecule encoding a protein of the present invention to produce the protein and (b) recovering the protein therefrom. Details on producing recombinant cells and culturing thereof are presented below. The phrase "recovering the protein" refers simply to collecting the whole fermentation medium containing the protein and need not imply additional steps of separation or purification. Proteins of the present invention can be purified using a variety of standard protein purification techniques, as heretofore disclosed.

Isolated proteins of the present invention are preferably retrieved in "substantially pure" form. As used herein, "substantially pure" refers to a purity that allows for the effective use of the protein as a vaccine. A vaccine for animals, for example, should exhibit no substantial toxicity and should be capable of stimulating the production of antibodies in a vaccinated animal.

Another embodiment of the present invention is an isolated nucleic acid molecule capable of hybridizing under stringent conditions with a gene encoding a flea protease present in a flea midgut. Such a nucleic acid molecule is also referred to herein as a flea protease nucleic acid molecule. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

As used herein, a flea protease gene includes all nucleic acid sequences related to a natural flea protease gene such as regulatory regions that control production of a flea protease protein encoded by that gene (such as, but not limited to, transcription, translation or post-translation control regions) as well as the coding region itself. A nucleic acid molecule of the present invention can be an isolated natural flea protease nucleic acid molecule or a homologue thereof. A nucleic acid molecule of the present invention can include one or more regulatory regions, full-length or partial coding regions, or combinations thereof. The minimal size of a flea protease nucleic acid molecule of the present invention is the minimal size capable of forming a stable hybrid under stringent hybridization conditions with a corresponding natural gene. Flea protease nucleic acid molecules can also include a nucleic acid molecule encoding a hybrid protein, a fusion protein, a multivalent protein or a truncation fragment.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions.

An isolated nucleic acid molecule of the present invention can also be produced using recombinant DNA technology (e.g., polymerase chain reaction (PCR) amplification, cloning) or chemical synthesis. Isolated flea protease nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a flea protease protein of the present invention or to form stable hybrids under stringent conditions with natural nucleic acid molecule isolates.

A flea protease nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an immune response against a flea protease and/or to have proteolytic activity) and/or by hybridization with isolated flea protease nucleic acids under stringent conditions.

An isolated flea protease nucleic acid molecule of the present invention can include a nucleic acid sequence that encodes at least one flea protease protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an flea protease protein.

One embodiment of the present invention is a flea protease nucleic acid molecule of the present invention that is capable of hybridizing under stringent conditions to a nucleic acid that encodes at least a portion of a flea protease or a homologue thereof. Preferred is a flea protease nucleic acid molecule that includes a nucleic acid sequence having at least about 65 percent, preferably at least about 75 percent, more preferably at least about 85 percent, and even more preferably at least about 95 percent homology with the corresponding region(s) of the nucleic acid sequence encoding at least a portion of a flea protease protein. Particularly preferred is a flea protease nucleic acid molecule capable of encoding at least a portion of a flea protease that naturally is present in flea midguts and preferably is included in a soluble flea midgut preparation of the present invention. Examples of nucleic acid molecules of the present invention are disclosed in the Examples section.

Knowing a nucleic acid molecule of a flea protease protein of the present invention allows one skilled in the art to make copies of that nucleic acid molecule as well as to obtain a nucleic acid molecule including additional portions of flea protease protein-encoding genes (e.g., nucleic acid molecules that include the translation start site and/or transcription and/or translation control regions), and/or flea protease nucleic acid molecule homologues. Knowing a portion of an amino acid sequence of a flea protease protein of the present invention allows one skilled in the art to clone nucleic acid sequences encoding such a flea protease protein. In addition, a desired flea protease nucleic acid molecule can be obtained in a variety of ways including screening appropriate expression libraries with antibodies which bind to flea protease proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or cDNA libraries can be used). To isolate flea protease nucleic acid molecules, preferred cDNA libraries include cDNA libraries made from unfed whole fleas, fed whole fleas, fed flea midguts, unfed flea midguts, and flea salivary glands. Techniques to clone and amplify genes are disclosed, for example, in Sambrook et al., ibid. The Examples section includes examples of the isolation of cDNA sequences encoding flea protease proteins of the present invention.

The present invention also includes nucleic acid molecules that are oligonucleotides capable of hybridizing, under stringent conditions, with complementary regions of other, preferably longer, nucleic acid molecules of the present invention that encode at least a portion of a flea protease protein. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit flea protease production. Such therapeutic applications include the use of such oligonucleotides in, for example, antisense-, triplex formation-, ribozyme- and/or RNA drug-based technologies. The present invention, therefore, includes such oligonucleotides and methods to interfere with the production of flea protease proteins by use of one or more of such technologies.

The present invention also includes a recombinant vector, which includes a flea protease nucleic acid molecule of the present invention inserted into any vector capable of delivering the nucleic acid molecule into a host cell. Such a vector contains heterologous nucleic acid sequences, that is nucleic acid sequences that are not naturally found adjacent to flea protease nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of flea protease nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell. Preferred nucleic acid molecules to include in recombinant vectors of the present invention are disclosed herein.

As heretofore disclosed, one embodiment of the present invention is a method to produce a flea protease protein of the present invention by culturing a cell capable of expressing the protein under conditions effective to produce the protein, and recovering the protein. A preferred cell to culture is a recombinant cell that is capable of expressing the flea protease protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a host cell are disclosed herein.

Suitable host cells to transform include any cell that can be transformed and that can express the introduced flea protease protein. Such cells are, therefore, capable of producing flea protease proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with bacterial (e.g., *E. coli*) and insect (e.g., Spodoptera) cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth, insect and mammalian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, *Heliothis zea* insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding a flea protease protein.

Expression vectors of the present invention may also contain secretory signals (i.e., signal segment nucleic acid sequences) to enable an expressed flea protease protein to be secreted from the cell that produces the protein. Suitable signal segments include a flea protease protein signal segment or any heterologous signal segment capable of directing the secretion of a flea protease protein, including fusion proteins, of the present invention. Preferred signal segments include, but are not limited to, flea protease, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of a flea protease nucleic acid molecule of the present invention can enhance the stability during production, storage and/or use of the protein encoded by the nucleic acid molecule. Furthermore, a fusion segment can function as a tool to simplify purification of a flea protease protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of a flea protease protein. Linkages between fusion segments and flea protease proteins can be constructed to be susceptible to cleavage to enable straightforward recovery of the flea protease proteins. Fusion proteins are preferably produced by culturing a recombinant cell transformed with a fusion nucleic acid sequence that encodes a protein including the fusion segment attached to either the carboxyl and/or amino terminal end of a flea protease protein.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed. A preferred recombinant molecule includes one or more nucleic acid molecules that encode one or more flea protease proteins, such as those disclosed herein.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce flea protease proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a flea protease protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant flea protease proteins may either remain within the recombinant cell; be secreted into the fermentation medium; be secreted into a space between two cellular membranes, such as the periplasmic space in *E. coli*; or be retained on the outer surface of a cell or viral membrane. Methods to purify such proteins are heretofore disclosed.

The present invention also includes isolated anti-flea protease antibodies and their use to reduce flea infestation on a host animal as well as in the environment of the animal. An anti-flea protease antibody is an antibody capable of selectively binding to a protease present in a flea midgut, including female and male fed midguts as well as female and male unfed midguts. An anti-flea protease antibody preferably binds to the protease in such a way as to reduce the proteolytic activity of that protease.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees. As used herein, the term "selectively binds to" refers to the ability of such antibodies to preferentially bind to the protease against which the antibody was raised (i.e., to be able to distinguish that protease from unrelated components in a mixture.). Binding affinities typically range from about $10^3$ $M^{-1}$ to about $10^{12}$ $M^{-1}$. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein used to obtain the antibodies. Antibodies of the present invention also include chimeric antibodies that can bind to more than one epitope. Preferred antibodies are raised in response to proteins that are encoded, at least in part, by a flea protease nucleic acid molecule of the present invention.

Anti-flea antibodies of the present invention include antibodies raised in an animal administered a flea protease vaccine of the present invention that exert their effect when fleas feed from the vaccinated animal's blood containing such antibodies. Anti-flea antibodies of the present invention also include antibodies raised in an animal against one or more flea protease proteins, or soluble flea midgut preparations, of the present invention that are then recovered from the animal using techniques known to those skilled in the art. Yet additional antibodies of the present invention are produced recombinantly using techniques as heretofore disclosed for flea protease proteins of the present invention. Antibodies produced against defined proteins can be advantageous because such antibodies are not substantially contaminated with antibodies against other substances that might otherwise cause interference in a diagnostic assay or side effects if used in a therapeutic composition.

Anti-flea protease antibodies of the present invention have a variety of uses that are within the scope of the present invention. For example, such antibodies can be used in a composition of the present invention to passively immunize an animal in order to protect the animal from flea infestation. Anti-flea antibodies can also be used as tools to screen expression libraries and/or to recover desired proteins of the present invention from a mixture of proteins and other contaminants. Furthermore, antibodies of the present invention can be used to target cytotoxic agents to fleas in order to kill fleas. Targeting can be accomplished by conjugating (i.e., stably joining) such antibodies to the cytotoxic agents using techniques known to those skilled in the art.

A preferred anti-flea protease antibody of the present invention can selectively bind to, and preferentially reduce the proteolytic activity of, a flea serine protease, a flea metalloprotease, a flea aspartic acid protease and/or a flea cysteine protease. More preferred anti-flea protease antibodies include anti-flea serine protease antibodies, anti-flea metalloprotease antibodies, and anti-flea aminopeptidase antibodies. Particularly preferred are anti-flea serine protease antibodies.

The present invention also includes the use of protease inhibitors that reduce proteolytic activity of flea proteases to reduce flea infestation of animals and the surrounding environment. As used herein, protease inhibitors are compounds that interact directly with a protease thereby inhibiting that protease's activity, usually by binding to or otherwise interacting with the protease's active site. Protease inhibitors are usually relatively small compounds and as such differ from anti-protease antibodies that interact with the active site of a protease.

Protease inhibitors can be used directly as compounds in compositions of the present invention to treat animals as long as such compounds are not harmful to the animals being treated. Protease inhibitors can also be used to identify preferred types of flea proteases to target using compositions of the present invention. For example, the inventors have shown herein the predominance of serine proteases in flea midguts, particularly in soluble flea midgut preparations, using protease inhibitors. Such knowledge suggests that effective reduction of flea infestation of an animal can be achieved using serine protease vaccines, anti-flea serine protease antibodies and other inhibitors of serine protease synthesis and activity that can be tolerated by the animal. That other proteases are also present in flea midguts according to the present invention also suggests targeting such proteases. Methods to use protease inhibitors are known to those skilled in the art; examples of such methods are disclosed herein.

In one embodiment, a protease inhibitor that can be used in a composition of the present invention to treat an animal is identified by a method including the following steps: (a) identifying candidate (i.e., putative, possible) inhibitor compounds by testing the efficacy of one or more protease inhibitors (i) in vitro for their ability to inhibit flea protease activity and/or (ii) in a flea feeding assay for their ability to reduce the survival and/or fecundity of fleas by adding the inhibitors to the blood meal of a flea being maintained, for example, in a feeding system, such as that described by Wade et al., 1988, *J.Med Entomol.* 25, 186–190; and (b) testing the efficacy of the candidate inhibitor compounds in animals infested with fleas. Although one does not need both in vitro assay data and flea feeding assay data to determine which candidate compounds to administer to animals, evaluation of both sets of data is preferred since data from neither of the assays necessarily predicts data to be obtained from the other assay. For example, candidate compounds identified using the in vitro assay may work "in the test tube" but may not work in vivo for a number of reasons, including the presence of interfering components in the blood meal that inhibit the activity of such compounds; e.g., although aprotinin can inhibit at least some flea serine proteases in vitro, aprotinin does not work well in the presence of serum proteins, such as are found in the blood. Furthermore, candidate inhibitor compounds identified by the flea feeding assays can include not only desired compounds but also compounds that reduce the viability and/or fecundity of fleas due to general toxicity (e.g., affecting the mitochondria of fleas).

In another embodiment, protease inhibitors are used in the purification of corresponding proteases by, for example, affinity chromatography, in which, a protease inhibitor is incubated with a mixture containing a desired protease under conditions that the inhibitor forms a complex with the protease. The protease can then be recovered from the complex. The protease inhibitor can be attached to a solid support and/or be labelled with, for example, a radioactive, fluorescent, or enzymatic tag that can be used to detect and/or recover the complex.

Suitable protease inhibitors to use in accordance with the present invention include serine protease inhibitors, metalloprotease inhibitors, aspartic acid protease inhibitors, cysteine protease inhibitors, and/or aminopeptidase inhibitors. Preferred protease inhibitors include serine protease inhibitors, metalloprotease inhibitors and aminopeptidase inhibitors, particularly those that are broad spectrum inhibitors. More preferred are broad spectrum serine protease inhibitors.

There is a wide variety of protease inhibitors, as is known to one skilled in the art. Examples include, but are not limited to, AEBSF, aprotinin, bestatin, chloromethyl ketones TLCK (Nα-p-tosyl-L-lysine chloromethyl ketone) and TPCK (N-tosyl-L-phenylalanine chloromethyl ketone), chymostatin, cystatin, 3'4-dichloroisocoumarin, E-64 (trans-epoxysuccinyl-L-leucylamido-(4-guanidino)butane), EDTA (ethylenediaminetetraacetic acid), leupeptin, methyl ketones having a variety of leaving groups, oxidized L-leucinethiol, pepstatin, 1,10-orthophenanthroline, phosphoramidon, soybean trypsin/chymotrypsin inhibitor and soybean trypsin inhibitor. Preferred protease inhibitors for use in the present invention include AEBSF, bestatin, E-64 leupeptin, pepstatin, 1,10-orthophenanthroline, posphoramidon, TLCK and TPCK, with AEBSF (a broad spectrum serine protease inhibitor), bestatin (an inhibitor of leucine aminopeptidase) and 1,10-orthophenanthroline (a broad spectrum metalloprotease inhibitor) being particularly preferred.

Protease inhibitors can be produced using methods known to those skilled in the art. Protein- or peptide-based protease inhibitors, such as cystatin or small peptides comprising a protease substrate, can be produced recombinantly and modified as necessary.

The present invention also includes the use of proteolytically active flea protease proteins of the present invention to identify additional protease inhibitors, and preferably protease inhibitor compounds that can be included in a composition of the present invention to be administered to animals. A method to identify a flea protease inhibitor includes the steps of (a) contacting (e.g., combining, mixing) an isolated flea protease protein with a putative (i.e., candidate) inhibitory compound under conditions in which, in the absence of the compound, the protein has proteolytic activity, and (b) determining if the putative inhibitory compound inhibits the proteolytic activity of the protein. Putative inhibitory compounds to screen include organic molecules, antibodies (including functional equivalents thereof) and substrate analogs. Methods to determine protease activity are known to those skilled in the art, as heretofore disclosed.

The present invention also includes a test kit to identify a compound capable of inhibiting flea protease activity. Such a test kit includes an isolated flea protease protein having proteolytic activity and a means for determining the extent of inhibition of proteolytic activity in the presence of (i.e., effected by) a putative inhibitory compound.

The present invention also includes inhibitors isolated by such a method, and/or test kit, and their use to inhibit any flea protease that is susceptible to such an inhibitor.

It is to be appreciated that the present invention also includes mimetopes of compounds of the present invention that can be used in accordance with methods as disclosed for compounds of the present invention. As used herein, a mimetope of a proteinaceous compound of the present invention (e.g., a flea protease protein, an anti-flea protease antibody, a proteinaceous inhibitor of protease activity or synthesis) refers to any compound that is able to mimic the activity of that proteinaceous compound, often because the mimetope has a structure that mimics the proteinaceous compound. For example, a mimetope of a flea protease protein is a compound that has an activity similar to that of an isolated flea protease protein of the present invention. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

The present invention includes therapeutic compositions, also referred to herein as compositions, that include a (i.e., at least one) compound of the present invention. Preferred compounds to include in a composition of the present invention include flea protease vaccines, anti-flea protease antibodies and/or protease inhibitors as disclosed herein. Such a therapeutic composition can protect an animal from flea infestation by reducing flea protease activity, thereby reducing flea burden on the animal and in the environment of the animal.

Another embodiment of the present invention is a therapeutic composition that includes a first compound that reduces flea protease activity and a second compound that reduces flea burden by a method other than by reducing flea protease activity. The present invention also includes a method to protect an animal from flea infestation by administering to the animal such a composition. The first compound of such a composition by effectively reducing flea protease activity in the midgut, enhances the activity of the second compound. While not being bound by theory, it is believed that a number of anti-flea treatments, particularly those that are proteinaceous, are not very effective because they are degraded in the flea midgut. The present invention permits the effective use of such anti-flea treatments by reducing proteolytic degradation of such treatments by the flea midgut.

Preferred first compounds to include in such a composition include flea protease vaccines, anti-flea protease antibodies and/or protease inhibitors as disclosed herein.

Suitable second compounds include any anti-flea agent(s), including, but not limited to, proteinaceous compounds, insecticides and flea collars. Preferred second compounds are proteinaceous compounds that effect active immunization (e.g., antigen vaccines), passive immunization (e.g., antibodies), or that otherwise inhibit a flea activity that when inhibited can reduce flea burden on and around an animal. Examples of second compounds include a compound that inhibits binding between a flea membrane protein and its ligand (e.g., a compound that inhibits flea ATPase activity or a compound that inhibits binding of a peptide or steroid hormone to its receptor), a compound that inhibits hormone (including peptide or steroid hormones) synthesis, a compound that inhibits vitellogenesis (including production of vitellin and transport and maturation thereof into a major egg yolk protein), a compound that inhibits fat body function, a compound that inhibits flea muscle action, a compound that inhibits the flea nervous system, a compound that inhibits the flea immune system and/or a compound that inhibits flea feeding.

Compositions of the present invention can also include other components such as a pharmaceutically acceptable excipient, an adjuvant, and/or a carrier. For example, compositions of the present invention can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a composition of the present invention into an animal. As used herein a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposcheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to reduce protease activity in fleas feeding from the animal over a period of time ranging from about 1 to about 12 months. A controlled release formulation of the present invention is capable of effecting a treatment for preferably at least about 1 month, more preferably at least about 3 months and even more preferably for at least about 6 months, even more preferably for at least about 9 months, and even more preferably for at least about 12 months.

In order to protect an animal from flea infestation, a therapeutic composition of the present invention is administered to the animal in an effective manner such that the protease activity of fleas feeding from the blood stream of animals treated with the composition is reduced. As such, a treated animal is an animal that is competent to reduce the flea burden by reducing flea protease activity, or by reducing flea protease activity and at least one other flea activity. Preferably, the protease activity is reduced by at least about 50 percent, more preferably by at least about 70 percent and even more preferably by at least about 90 percent. Methods to administer compositions to the animal in order to render the animal competent depend on the nature of the composition and administration regime.

Animals administered a protease vaccine with at least one booster shot usually become competent at about the same time as would be expected for any vaccine treatment. For example, animals administered a booster dose about 4 to 6 weeks after a primary dose usually become competent within another about 3 to 4 weeks. Animals administered a composition including an anti-flea protease antibody or protease inhibitor become competent as soon as appropriate serum levels of the compound are achieved, usually with one to three days.

In a preferred embodiment, a composition of the present invention when administered to a host animal is able to reduce flea viability by at least about 50 percent within at least about 21 days after the fleas begin feeding from the treated animal. (Note that fleas usually live about 40 days to about 50 days on one or more animals.) A more preferred composition when administered to a host animal is able to reduce flea viability by at least about 65 percent within at least about 14 days after the fleas begin feeding from the treated animal. An even more preferred composition when administered to an animal is able to reduce flea viability by at least about 90 percent within at least about 7 days after the fleas begin feeding from the treated animal.

In another preferred embodiment, a composition of the present invention when administered to a host animal is able to reduce flea fecundity (i.e., egg laying ability) by at least about 50 percent, more preferably by at least about 70 percent, and even more preferably by at least about 90 percent, within at least about 30 days after the fleas begin feeding from the treated animal. (Note that fleas usually do not begin laying eggs until about 7 days after taking a blood meal.)

In accordance with the present invention, compositions are administered to an animal in a manner such that the animal becomes competent to reduce flea protease activity in a flea that feeds from the competent; i.e., the animal becomes a treated animal. For example, a flea protease vaccine of the present invention, when administered to an animal in an effective manner, is able to elicit (i.e., stimulate) an immune response that produces an antibody titer in the blood stream of the animal sufficient to reduce flea protease activity. Similarly, an anti-flea protease antibody of the present invention, when administered to an animal in an effective manner, is administered in an amount so as to be present in the animal's blood stream at a titer that is sufficient to reduce flea protease activity. A protease inhibitor compound of the present invention, when administered to an animal in an effective manner, is administered in a manner so as to be present in the animal's blood stream at a concentration that is sufficient to reduce flea protease activity. oligonucleotide nucleic acid molecules of the present invention can also be administered in an effective manner, thereby reducing expression of flea proteases.

Compositions of the present invention can be administered to animals prior to or during flea infestation. It is to be noted that when vaccines of the present invention are administered to an animal, a time period is required for the animal to elicit an immune response before the animal is competent to inhibit protease activity of fleas feeding from that animal. Methods to obtain an immune response in an animal are known to those skilled in the art.

Acceptable protocols to administer compositions in an effective manner include individual dose size, number of doses, frequency of dose administration, and mode of administration. Determination of such protocols can be accomplished by those skilled in the art. A suitable single dose is a dose that is capable of protecting an animal from flea infestation when administered one or more times over a suitable time period. For example, a preferred single dose of a protease vaccine or a mimetope thereof ranges from about 1 microgram (µg, also denoted ug) to about 10 milligrams (mg) of the composition per kilogram body weight of the animal. Booster vaccinations can be administered from about 2 weeks to several years after the original administration. Booster vaccinations preferably are administered when the immune response of the animal becomes insufficient to protect the animal from flea infestation. A preferred administration schedule is one in which from about 10 µg to about 1 mg of the vaccine per kg body weight of the animal is administered from about one to about two times over a time period of from about 2 weeks to about 12 months. In one embodiment, a booster dose of a composition of the present invention is administered about 4 to 6 weeks after the primary dose, and additional boosters are administered about once or twice a year. Modes of administration can include, but are not limited to, oral, nasal, topical, transdermal, rectal, and parenteral routes. Parenteral routes can include, but are not limited to subcutaneous, intradermal, intravenous, and intramuscular routes.

In another embodiment, a preferred single dose of an anti-flea protease antibody composition or a mimetope thereof ranges from about 1 μg to about 10 mg of the composition per kilogram body weight of the animal. Anti-flea antibodies can be re-administered from about 1 hour to about biweekly for several weeks following the original administration. Booster treatments preferably are administered when the titer of antibodies of the animal becomes insufficient to protect the animal from flea infestation. A preferred administration schedule is one in which from about 10 μg to about 1 mg of an anti-flea protease antibody composition per kg body weight of the animal is administered about every 2 to every 4 weeks. Suitable modes of administration are as disclosed herein and are known to those skilled in the art.

According to one embodiment, a nucleic acid molecule of the present invention can be administered to an animal in a fashion to enable expression of that nucleic acid molecule into a protective protein (e.g., flea protease vaccine, anti-flea protease antibody, or proteinaceous protease inhibitor) or protective RNA (e.g., antisense RNA, ribozyme or RNA drug) in the animal to be protected from disease. Nucleic acid molecules can be delivered to an animal in a variety of methods including, but not limited to, (a) direct injection (e.g., as "naked" DNA or RNA molecules, such as is taught, for example in Wolff et al., 1990, *Science* 247, 1465–1468) or (b) packaged as a recombinant virus particle vaccine or as a recombinant cell vaccine (i.e., delivered to a cell by a vehicle selected from the group consisting of a recombinant virus particle vaccine and a recombinant cell vaccine).

A recombinant virus particle vaccine of the present invention includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses.

When administered to an animal, a recombinant virus particle vaccine of the present invention infects cells within the immunized animal and directs the production of a protective protein or RNA nucleic acid molecule that is capable of protecting the animal from disease caused by a parasite of the present invention. A preferred single dose of a recombinant virus particle vaccine of the present invention is from about $1 \times 10^4$ to about $1 \times 10^7$ virus plaque forming units (pfu) per kilogram body weight of the animal. Administration protocols are similar to those described herein for protein-based vaccines.

A recombinant cell vaccine of the present invention includes recombinant cells of the present invention that express at least one protein of the present invention. Preferred recombinant cells include Salmonella, *E. coli*, Mycobacterium, *S. frugiperda*, baby hamster kidney, myoblast G8, COS, MDCK and CRFK recombinant cells, with Salmonella recombinant cells being more preferred. Such recombinant cells can be administered in a variety of ways but have the advantage that they can be administered orally, preferably at doses ranging from about $10^8$ to about $10^{12}$ bacteria per kilogram body weight. Administration protocols are similar to those described herein for protein-based vaccines. Recombinant cell vaccines can comprise whole cells or cell lysates.

Compositions of the present invention can be administered to any animal susceptible to flea infestation, including warm-blooded animals. Preferred animals to treat include mammals and birds, with cats, dogs, humans, cattle, chinchillas, ferrets, goats, mice, minks, rabbits, raccoons, rats, sheep, squirrels, swine, chickens, ostriches, quail and turkeys as well as other furry animals, pets and/or economic food animals, being more preferred. Particularly preferred animals to protect are cats and dogs.

The present invention includes compositions to treat flea infestation by any flea. As such, compositions of the present invention can be derived from any flea species. Preferred fleas to target include fleas of the following genera: Ctenocephalides, Cyopsyllus, Diamanus (Oropsylla), Echidnophaga, Nosopsyllus, Pulex, Tunga, and Xenopsylla, with those of the species *Ctenocephalides canis*, *Ctenocephalides fells*, *Diamanus montanus*, *Echidnophaga gallinacea*, *Nosopsyllus faciatus*, *Pulex irritans*, *Pulex simulans*, *Tunga penetrans* and *Xenopsylla cheopis* being more preferred. Particularly preferred fleas from which to protect animals include fleas of the species *Ctenocephalides fells*, *Ctenocephalides canis*, and *Pulex species* (e.g., *Pulex irritans* and *Pulex simulans*). It is also within the scope of the present invention to administer compositions of the present invention directly to fleas.

The present invention also includes the use of compositions of the present invention to reduce infestation by other ectoparasites as well as the use of compositions including protease vaccines, anti-protease antibodies and compounds that inhibit protease synthesis and/or activity derived from any ectoparasite to reduce ectoparasite infestation, particularly controlled release formulations containing such compositions. Preferred ectoparasites to target include arachnids, insects and leeches. More preferred ectoparasites to target include fleas; ticks, including both hard ticks of the family Ixodidae (e.g., Ixodes and Amblyomma) and soft ticks of the family Argasidae (e.g., Ornithodoros, such as *O. parkeri* and *O. turicata*); flies, such as midges (e.g., Culicoides), mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs, including those carrying Chagas disease. Even more preferred ectoparasites to target include fleas, mosquitos, midges, sandflies, blackflies, ticks and Rhodnius.

The following examples are provided for the purposes of illustration and are not intended to limit the scope of the present invention.

EXAMPLES

Examples 1

This Example demonstrates that soluble flea midgut preparations contain serine protease activity as well as leucine aminopeptidase activity.

Using a homogenization/sonication protocol as described in Ser. No. 07/806,482, ibid., followed by an about 2 minute centrifugation step at about 10,000×g, soluble flea midgut preparations were obtained from fed and unfed fleas. Pellets from the centrifugation step were also collected and resuspended for analysis. Also prepared were whole flea lysates. Peptide substrate screening studies using the synthetic chromogenic trypsin substrate BAPNA (Nα-benzoyl-DL-arginine-p-nitroanilide; available from Sigma Chemical Co., St. Louis Mo.) demonstrated significant proteolytic activity in both soluble flea midgut preparations as well as some proteolytic activity in resuspended midgut pellets. Soluble unfed flea midgut preparations exhibited about 10 times as much activity as did controls (samples to which no flea midgut fractions were added), whereas soluble fed flea midgut preparations exhibited about 20 times as much activity as did controls. Whole flea preparations exhibited about 2 to 3 times as much activity as did controls.

The ability of soluble fed and unfed flea midgut preparations to cleave BAPNA was almost completely inhibited (i.e., nearly 100%) by aprotinin (available from Sigma), whereas PMSF (phenylmethane-7-sulfonyl fluoride; available from Sigma) inhibited such proteolytic activity by about 50%. EDTA inhibited proteolytic activity of the preparations by about 10%, whereas addition of calcium ions stimulated proteolytic activity by about 25%. These results indicate the presence of serine protease activity, and more particularly of trypsin-like activity, in these soluble flea midgut preparations. These results also suggest the presence of serine protease isoforms in the preparations. It is also of interest to note that flea trypsin-like activity appears to be distinctive from that of mosquitos in that mosquito trypsins are not affected by EDTA or calcium ions.

Using a methyl-hemoglobin substrate, the pH optimum of the proteolytic activity in the soluble flea midgut preparations was found to be between pH 7 and pH 9, with a pH of about pH 8 giving the best activity. Such pH optima suggest the presence of serine proteases in soluble flea midgut preparations.

Soluble preparations of both unfed and fed flea midgut soluble preparations also were able to cleave the leucine aminopeptidase specific substrate LPNA (L-leucine-p-nitroanilide; available from Sigma) using standard conditions, indicating the presence of leucine aminopeptidase (LAP) activity in such preparations.

Example 2

The following example evaluated the number of proteases in flea midguts that could be assessed by protease substrate gel analysis.

Protease substrate gels (available from Novex, San Diego, Calif. as Novex Zymogels) were 10% polyacrylamide-SDS gels with 0.1% gelatin. Samples and gels were processed according to Novex instructions. Briefly, samples were diluted in SDS-PAGE sample buffer without reducing agents. Tris-glycine SDS-PAGE was carried out by standard procedures. After electrophoresis, gels were incubated in 0.25% Triton X-100 at room temperature for 30 minutes (min), then in developing buffer (50 mM (millimolar) Tris-HCl pH 7.0, 5 mM $CaCl_2$, 0.02% Brij 35, 0.2M (molar) NaCl) at room temperature for 30 min, and then incubated with fresh developing buffer at 37° C., usually overnight. Gels were then stained 30 min in 0.5% coomassie R-250, 40% methanol, 10% acetic acid and destained in 40% methanol, 10% acetic acid.

The following flea midguts were dissected directly into sample buffer: 100 midguts from unfed males; 100 midguts from unfed females; 100 midguts from fed males; and 100 midguts from fed females. Samples containing 10 or 20 midguts each were evaluated using protease substrate gel analysis and numerous negative staining bands were observed. The general pattern was the same for female and male midguts, although there appeared to be more activity in gel lanes containing female midguts. There were distinct differences noted between gel lanes containing fed and unfed midguts. There was a definite increase in overall activity in the fed midgut lanes, and, in addition, there were differences in the band patterns.

Fed and unfed female midguts were further evaluated using protease substrate gel analysis and the results are shown in FIG. 1. The protease substrate gel shown in FIG. 1 demonstrates the relative proteolytic activity in 1, 2, 5 or 10 midguts from either fed or unfed female fleas. Specifically, lane 1 contains a set of molecular weight markers. Lanes 2 through 5 contain, respectively, 10, 5, 2 and 1 unfed midguts. Lanes 6 through 9 contain, respectively, 1, 2, 5 and 10 fed midguts. Lane 10 contains 100 µg of dried bovine blood.

Proteolytic activity could easily be detected in one fed or one unfed female midgut, although there was considerably more activity in the fed midgut. Lane 10 evaluated 100 µg of dried bovine blood to assess if the increase in activity seen in the fed midgut lane was due to proteases in the blood meal. No activity was seen in the blood lane.

Example 3

This example evaluated the protease classes present in flea midguts.

Three unfed female midguts and 0.75 fed female midguts were evaluated in duplicate in several protease substrate gels. Each gel was cut in half. Half was processed as described in Example 2, while the other half contained protease inhibitors in all incubation buffers. The following inhibitors were evaluated:

(a) the serine protease inhibitor AEBSF (available from Boehringer Mannheim, Indianapolis, Ind.) was used at a final concentration of 1 mM;

(b) the serine protease inhibitor soybean trypsin inhibitor (available from Sigma) was used at a final concentration of 100 µg/ml (milliliter);

(c) the cysteine and serine protease inhibitor leupeptin (available from Sigma) was used at a final concentration of 10 µg/ml;

(d) the aminopeptidase inhibitor bestatin (available from Sigma) was used at a final concentration of 0.25 mM;

(e) the metalloprotease inhibitor EDTA (available from Sigma) was used at a final concentration of 2 mM; and (f) the cysteine protease E-64 (available from Sigma) was used at a final concentration of 10 µg/ml.

Figure 2:
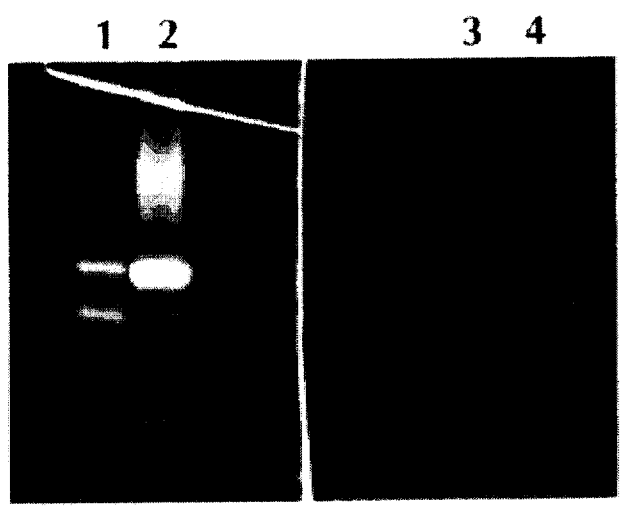
FIG. 2 depicts a protease substrate gel analysis of fed and unfed midgut preparations incubated in the presence or absence of a serine protease inhibitor.

AEBSF, soybean trypsin inhibitor and leupeptin were the only inhibitors to have any effect at the sensitivity of this assay. It was determined that serine proteases were the predominant, if not only, proteases present in the midgut preparations evaluated. FIG. 2 shows a protease substrate gel with fed (lanes 2 and 4) and unfed (lanes 1 and 3) midgut preparations with (lanes 3 and 4) and without (lanes 1 and 2) AEBSF. Residual activity in the inhibitor lanes could have been due to proteolysis that occurred during electrophoresis and prior to saturation of the gel with inhibitor in the incubation buffers.

Example 4

This Example evaluates protease activity contained in a soluble fed midgut preparation of the present invention.

Figure 3:
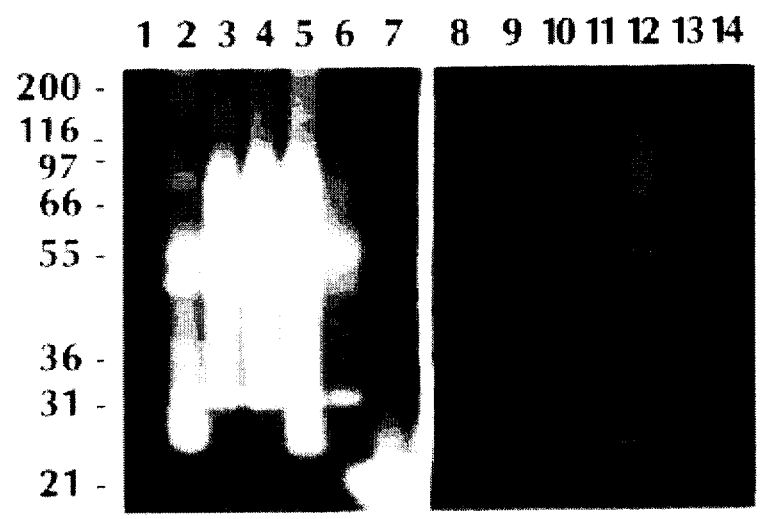
FIG. 3 depicts a protease substrate gel analysis of various fractions obtained in the preparation of a soluble flea midgut preparation incubated in the presence or absence of a serine protease inhibitor.

Mixed-sex fed flea midguts were processed as described in Ser. No. 07/806,482, ibid. Aliquots of several steps of the procedure were evaluated by loading an equivalent of 0.4 midguts per lane of a protease substrate gel as described in Example 2. The results are shown in FIG. 3. Samples were from the low speed supernatant (lanes 2 and 9), sonicated midguts (lanes 3 and 10), high speed supernatant (lanes 4 and 11), combined low and high speed supernatants (FGS) (lanes 5 and 12) and the high speed pellet (lanes 6 and 13). Lanes 7 and 8 contained 50 nanograms (ng) of trypsin as a control. Duplicate lanes were evaluated. The gel was cut in half, and lanes 1-7 were processed as described in Example 2, and lanes 8-14 were processed with 100 µg/ml soybean trypsin inhibitor in all the incubation buffers.

Protease activity was seen in all preparations, the most being observed in the FGS lane (lane 5). It was also evident that the majority of the activity was inhibited by soybean trypsin inhibitor, a serine protease inhibitor.

Example 5

This Example demonstrates the increase in flea midgut protease activity after blood feeding by fleas.

Figure 4:
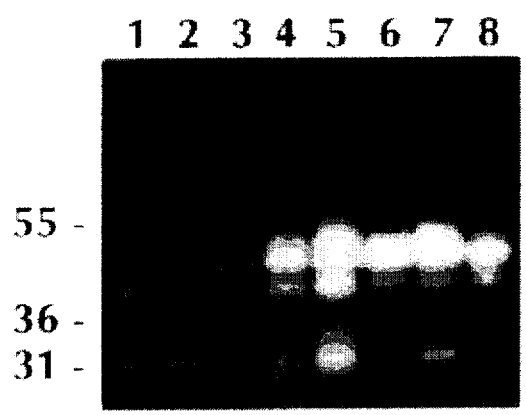
FIG. 4 depicts a protease substrate gel showing midgut protease activity as a function of time after flea blood feeding.

Fleas were fed on a dog for 15 minutes. At timed intervals after feeding, two midguts were dissected directly into sample buffer and proteases evaluated by protease substrate gel analysis as described in Example 2. FIG. 4 depicts a gel showing midgut protease activity at 30 min (lane 1), 1 hr (lane 2), 2 hr (lane 3), 4 hr (lane 4), 6 hr (lane 5), 8 hr (lane 6), 24 hr (lane 7) and 56 hr (lane 8) after blood feeding ended.

Increases in proteolytic activity were first observed 2 hr (lane 3) after feeding, although at 4 hr (lane 4) there was a much greater increase in activity noted. This increase in activity was still noticed 56 hr after feeding (lane 8).

Example 6

This Example evaluates the effect of a number of protease inhibitors on flea viability and fecundity in a flea feeding system as described by Wade et al. ibid.

The following protease inhibitors were tested at the indicated final concentrations in blood meals:

(a) Aminopeptidase inhibitor bestatin at 1.3 mM and 13 mM;

(b) Aspartic acid protease inhibitor pepstatin A at 1 μg/ml and 10 μg/ml;

(c) Cysteine protease inhibitor E-64 at 1 μg/ml and 10 μg/ml. (d) Metalloprotease inhibitor phosphoramidon at 10 μg/ml and 100 μg/ml; and (e) the following serine protease inhibitors:
AEBSF at 0.3 mM, 0.5 mM, 5.0 mM and 6.0 mM;
Aprotinin at 2 μg/ml and 20 μg/ml;
Leupeptin at 5 μg/ml and 50 μg/ml;
Soybean trypsin inhibitor at 10 μg/ml and 100 μg/ml;
Soybean trypsin/chymotrypsin inhibitor at 10 μg/ml and 100 μg/ml;

AEBSF is available from Boehringer Mannheim; all other listed inhibitors are available from Sigma.

Protease inhibitor compounds were tested in groups of 3 to 6 including appropriate control groups. Inhibitors were not tested in groups of common inhibition types. Rather, they were tested in groups based on the diluent needed to dissolve them. (AEBSF, aprotinin, bestatin, leupeptin, phosphoramidon, soybean trypsin inhibitor and soybean trypsin/chymotrypsin inhibitor were dissolved in water; E-64 and pepstatin were dissolved in ethanol). This reduced the number of control (diluent only) groups needed within a particular assay. Inhibitor concentrations were chosen such that the lower concentration used was within the range recommended by the supplier for that inhibitor. The higher concentration was typically 10 times above the lower concentration and was used to look for dose response.

The general protocol for all of the assays was as follows: Approximately 2000 newly emerged adult fleas were placed in feeding chambers to feed on normal blood for about 24 to 48 hr. The fleas were prefed for two reasons: The first was to be certain that only fleas that would feed in the feeding system were used in the comparative study. The second was to prime female fleas for egg laying, since female fleas typically do not begin laying maximal numbers of eggs per day until the third day of feeding.

The prefed fleas were placed in "minifeeder" feeding chambers at a ratio of about 80 female fleas to about 20 male fleas for a total of about 100 fleas per chamber. Actual total number of fleas per chamber varied from about 90 to 125 fleas. Previous experiments have not demonstrated any differences in adult survival or fecundity based on such variance in numbers of fleas in a chamber. Three chambers were prepared for each experimental and control group. A fresh blood meal containing the appropriate inhibitor in 3 ml total volume was placed on each chamber daily through the 7 day extent of an assay.

On days 3, 5, and 7 of the assay, surviving adult fleas were transferred to clean chambers. The contents of the original chambers were dissolved in about 40 ml of PBS (phosphate-buffered saline) in a 50 ml Falcon tube. The contents of a given tube were then filtered through a pre-weighed #1 Whatman filter disk inserted into a vacuum filter. The 50 ml tube and the filter funnel were rinsed with distilled water which was then passed through the filter. Once the chamber contents had been filtered, dead adult fleas were removed from the filter paper and placed in a labelled tube so that they could be counted and sexed. The filter paper was then placed into a preweighed 12×75 polypropylene tube and dried in the SpeedVac for 2.5 hr with the heater on. After drying the filter paper was weighed. The weight of the filter paper and tube was subtracted to obtain the dry weight of the eggs and this value was converted to an estimated number of eggs using the formula $y=41384.361x=162.37$, where x=dry weight of eggs.

On day 7, adult fleas that had survived the study were frozen, counted and sexed. The numbers were added to the number of male and female fleas that had died during the assay to verify the number of male and female fleas in each chamber at the start of the study.

Female, male and total adult flea survival were calculated for all experimental and control groups on days 3, 5, and 7 of each assay. Additionally, the number of eggs per surviving female was calculated on days 3, 5 and 7. Female fleas found dead on a given collection date were included in the total number of egg-laying females for the days between that date and the previous collection date, providing a conservative estimate of fecundity. Fecundity values were averaged for the three collection dates to obtain an average for each group over 7 days.

Results of these studies are presented below in Table 1 and FIG. 6 through FIG. 9. All survival and fecundity values are presented below as a percent of control value.

TABLE 1

Effect of Protease Inhibitors on Flea Viability and Fecundity

| Compound | Conc. | Fecundity[1] Days 1–7 | Adult Survival[1] Female | Male | Total |
|---|---|---|---|---|---|
| AEBSF | | | | | |
| | 6.0 mM | 17.2% | 4.1% | 0.0 | 3.4% |
| | 5.0 mM | 1.4% | 6.8% | 0.0% | 5.6% |
| | 0.5 mM | 95.0% | 103.9% | 104.2% | 103.6% |
| | 0.3 mM | 82.4% | 116.2% | 103.0% | 111.9% |
| Aprotinin | | | | | |
| | 20 ug/ml | 84.2% | 100.0% | 101.7% | 99.9% |
| | 2 ug/ml | 83.2% | 103.2% | 104.9% | 103.3% |

TABLE 1-continued

Effect of Protease Inhibitors
on Flea Viability and Fecundity

| Compound | Conc. | Fecundity[1] Days 1-7 | Adult Survival[1] Female | Male | Total |
|---|---|---|---|---|---|
| Leupeptin | | | | | |
| | 50 ug/ml | 77.6% | 101.5% | 111.7% | 104.6% |
| | 5 ug/ml | 85.0% | 71.0% | 61.4% | 68.4% |
| Soybean Trypsin Inhibitor | | | | | |
| | 100 ug/ml | 79.1% | 76.5% | 76.0% | 76.3% |
| | 10 ug/ml | 96.1% | 80.1% | 101.7% | 83.9% |
| Trypsin/Chymotrypsin Inhibitor | | | | | |
| | 100 ug/ml | 81.1% | 88.0% | 95.4% | 89.9% |
| | 10 ug/ml | 100.7% | 115.1% | 143.5% | 120.7% |
| E-64 | | | | | |
| | 10 ug/ml | 177.4% | 110.2% | 139.0% | 114.2% |
| | 1 ug/ml | 109.4% | 99.9% | 102.9% | 100.1% |
| | 10 ug/ml | 84.1% | 90.2% | 91.1% | 90.6% |
| | 1 ug/ml | 95.2% | 77.3% | 80.0% | 77.5% |
| Phosphoramidon | | | | | |
| | 100 ug/ml | 84.9% | 70.2% | 64.6% | 69.7% |
| | 10 ug/ml | 89.0% | 98.8% | 95.2% | 97.8% |
| PepstatinA | | | | | |
| | 10 ug/ml | 83.9% | 113.6% | 133.4% | 116.2% |
| | 1 ug/ml | 67.7% | 77.6% | 96.6% | 80.5% |
| Bestatin | | | | | |
| | 13.0 mM | 23.3% | 121.0% | 103.4% | 117.0% |
| | 1.3 mM | 60.4% | 119.5% | 116.3% | 116.8% |

[1]All experimental values are expressed as a percent of the corresponding control group.

The aminopeptidase inhibitor bestatin caused a significant (p<0.05) reduction in fecundity at 13 mM (77% reduction) and at 1.3 mM (40% reduction) indicating the presence of an aminopeptidase or other exopeptidase in flea midguts. Bestatin at the concentrations tested, however, had no significant effect on adult viability at either concentration. These results suggest that aminopeptidases may play a role in ovarian function, or a related process, such as vitellogenesis.

The aspartic acid protease inhibitor pepstatin A caused a significant reduction (p<0.05) in fecundity at 1 μg/ml (32% reduction), but not at 10 μg/ml. Pepstatin A had no significant effect on adult viability at either concentration.

The cysteine protease inhibitor E-64 showed no statistically significant reduction in fecundity in this assay. There was a small, but significant (p<0.05), reduction in total adult flea survival when E-64 was dissolved in grain alcohol and added to blood at 1 μg/ml. However, this reduction was not evident in the group that was fed blood containing 10 μg/ml E-64 in grain alcohol.

The metalloprotease inhibitor phosphoramidon caused a reduction in adult viability of about 30%, which, however was not statistically significant. There was no significant reduction in fecundity. Results using serine protease inhibitors were particularly interesting and suggest the significance of serine proteases in flea midguts. AEBSF administered at concentrations ranging from about 5 mM to about 6 mM reduced flea fecundity by more than 80%. In addition, adult survival was reduced to near zero (p<0.05).

Aprotinin, however, had no significant effect on either fecundity or viability, likely due to the ability of serum proteins, such as albumin, to interfere with aprotinin's inhibitory activity.

Leupeptin had no effect on fecundity at both concentrations, but reduced adult viability by 30% at 5 μg/ml. However, adult viability was not affected by 50 μg/ml leupeptin and none of the observed reductions were statistically significant.

Soybean trypsin inhibitor caused a small (20%) statistically insignificant reduction in fecundity at 100 μg/ml. The lower concentration had no effect. Soybean trypsin inhibitor, on the other hand, is very effective in in vitro studies as disclosed in several of the examples and was used to purify serine proteases as disclosed in Example 7. Soybean trypsin/chymotrypsin inhibitor had no effect on adult viability or fecundity.

Example 7

This Example describes the production of a preferred soluble flea midgut preparation of the present invention and purification of flea serine proteases therefrom. Also included is amino acid sequence analysis of a flea serine protease of the present invention.

The soluble flea midgut preparation was prepared as follows. Flea midguts (3,735) from a mix of female and male fed fleas were homogenized in a homogenization buffer comprising 1.5 ml 50 mM Tris-HCl, 0.5M NaCl, pH 8.5. The homogenate was centrifuged at 14,000×g for 10 min. The resultant pellet was processed again in another 1.5 ml of the homogenization. The two supernatant solutions were combined to form the soluble flea midgut preparation.

The preparation was added to 3 ml of p-aminobenzamidine-sepharose 6 B (affinity matrix for trypsin-like proteases, available from Sigma) and incubated at 5° C. overnight on a rocker. The sepharose beads were drained and washed with 7.5 ml of the homogenization buffer. The adsorbed proteins were eluted with 5 ml 0.1M p-aminobenzamidine in the same buffer. This eluate was concentrated and the buffer exchanged to 50 mM Tris-HCl pH 8.5, 0.1 mM $CaCl_2$ by ultrafiltration through a membrane with a 3 kD cutoff, the final volume being 140 μl (microliters).

Labeling of proteins was performed by adding 10 μl of (1,3-$^3$H)-diisopropylfluorophosphate (available from New England Nuclear, Beverly, Mass. at 6.0 Ci (Curies)/mmole, 1.0 mCi/ml) to 90 μl of the affinity purified proteins and incubating at 5° C. for 18 hours. The reaction was divided in half, each half then being separated by C4 reverse phase chromatography according to the following protocol:

Buffer A: 0.1% TFA in water

Figure 5A:
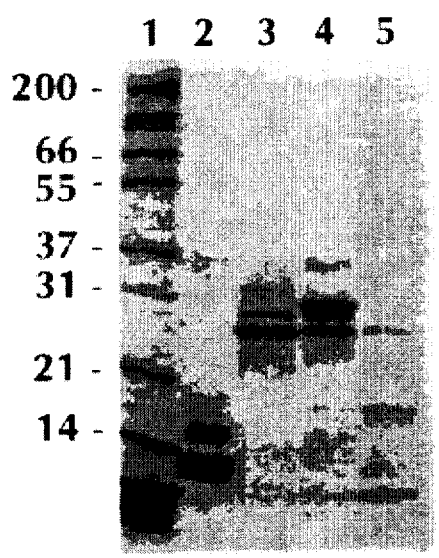
FIG. 5A depicts a coomassie stained SDS-PAGE of partially purified (1,3-$^3$H)-diisopropylfluoro-phosphate-labeled fed flea midgut serine proteases.
Figure 5B:
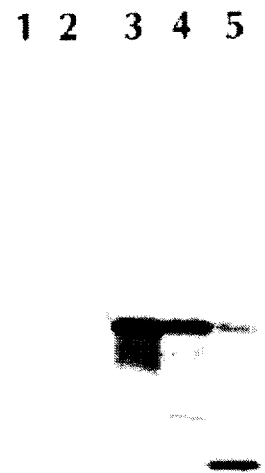
FIG. 5B depicts an autoradiogram of the SDS-PAGE gel of FIG. 5A of partially purified (1,3-$^3$H)-diisopropylfluoro-phosphate-labeled fed flea midgut serine proteases.
Figure 6:
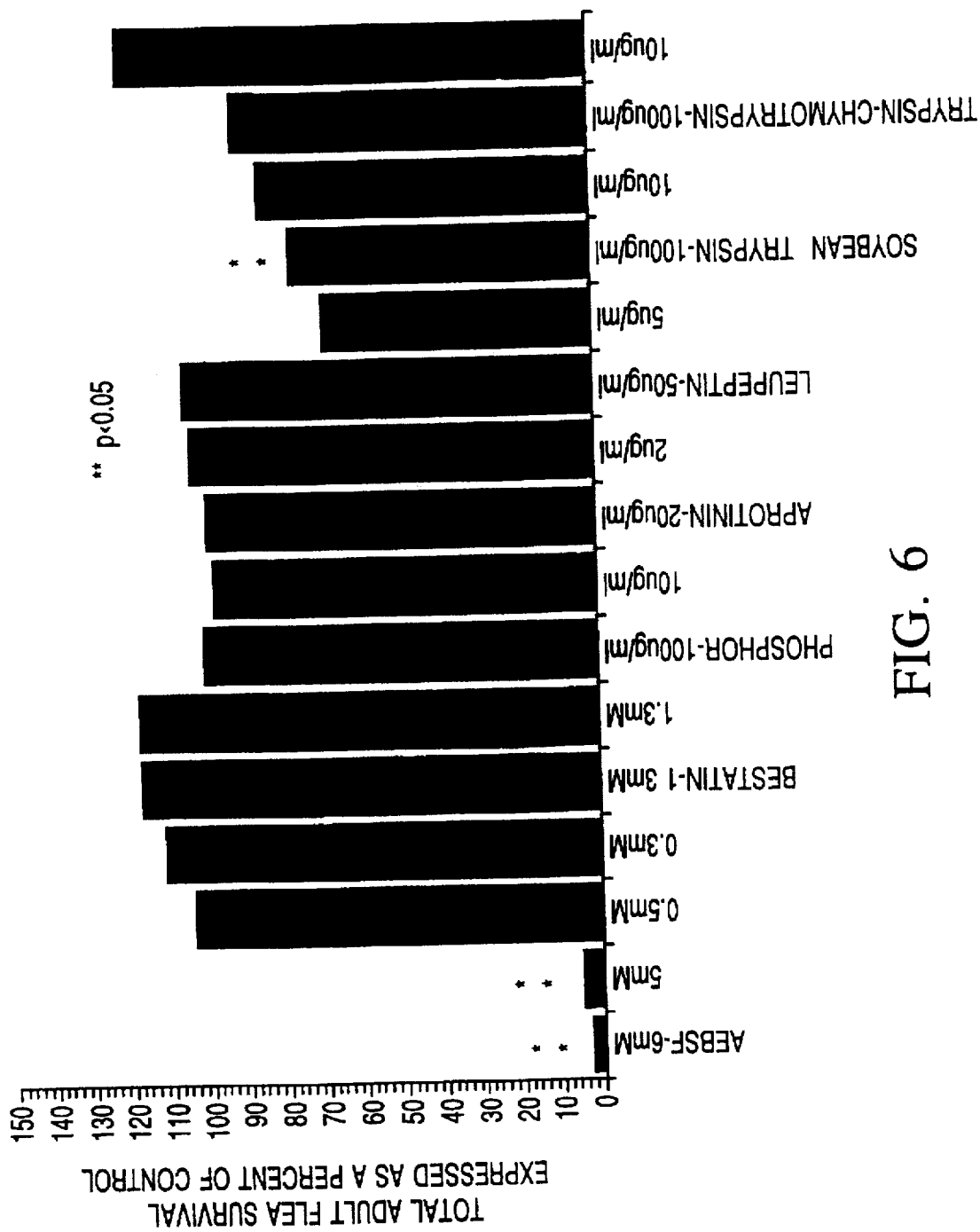
FIG. 6 depicts the mean viability of adult (both male and female) fleas fed blood containing certain protease inhibitors.
Figure 7:
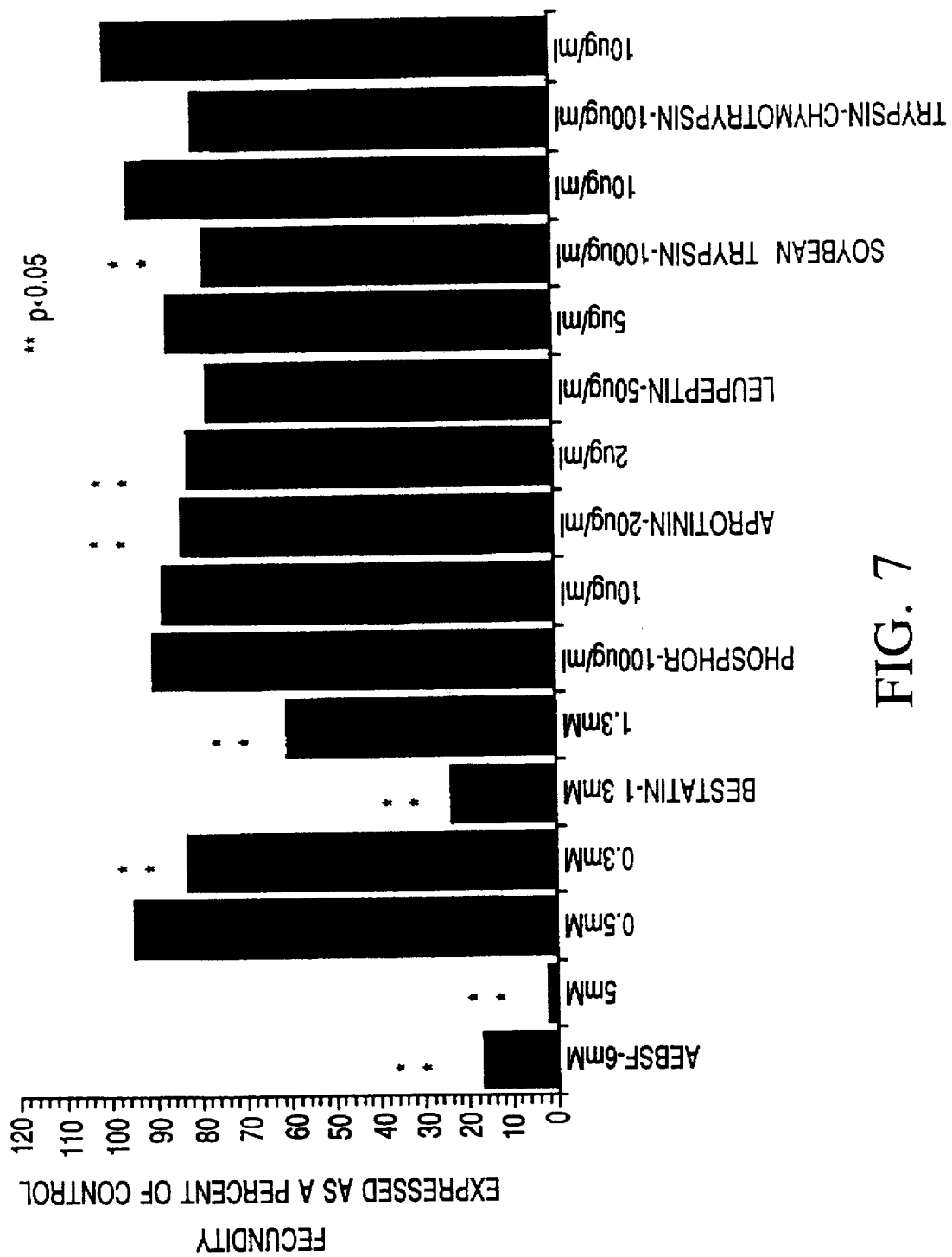
FIG. 7 depicts the mean fecundity of adult female fleas fed blood containing certain protease inhibitors.
Figure 8:
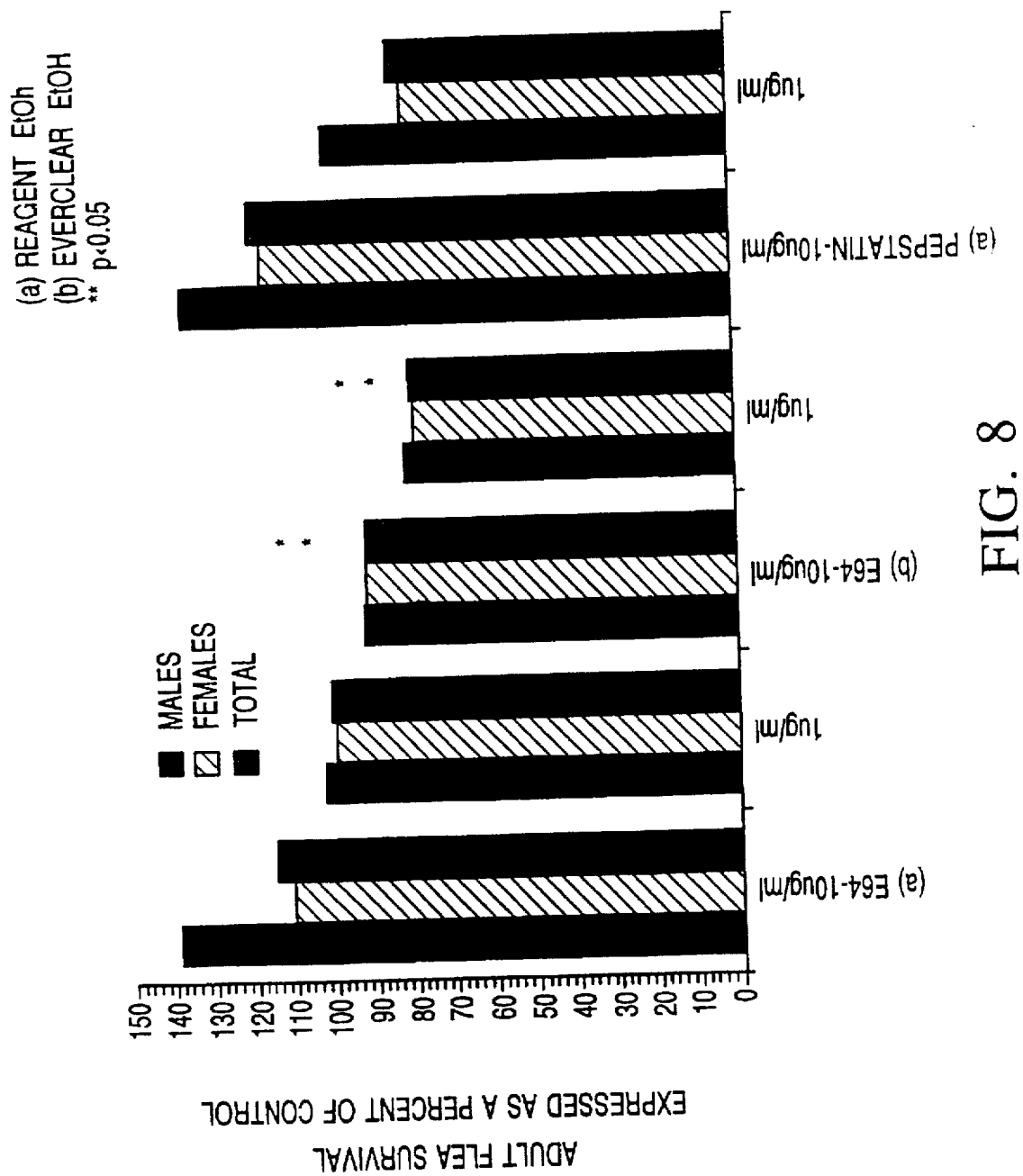
FIG. 8 depicts the mean viability of adult (both male and female) fleas fed blood containing certain protease inhibitors.
Figure 9:
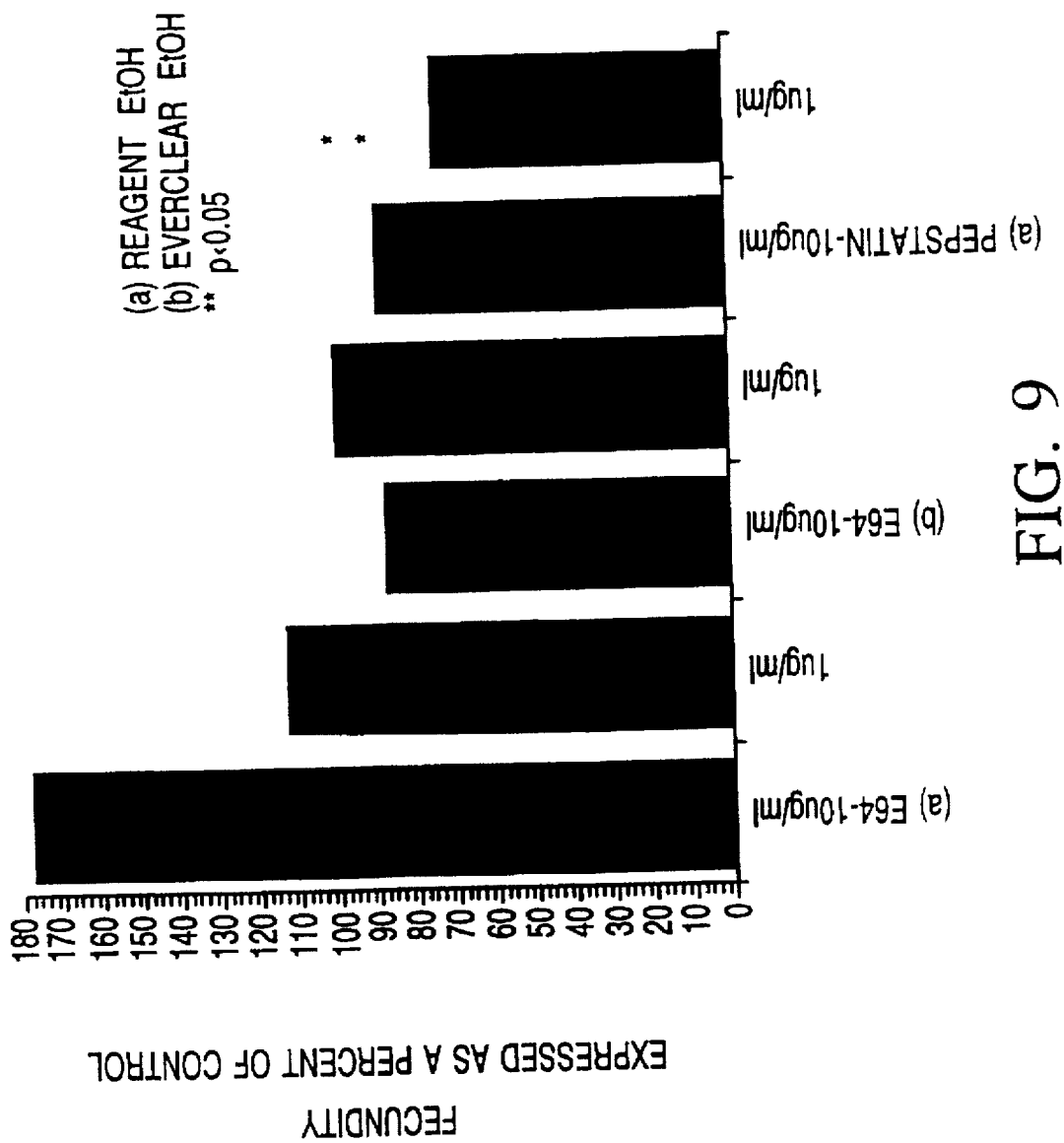
FIG. 9 depicts the mean fecundity of adult female fleas fed blood containing certain protease inhibitors.

Buffer B: 0.085% TFA, 90% Acetonitrile 0.8 ml/min, 220 nm, 1 min fractions 5.6% B 15 min 5.6% to 100% B over 60 min Ten microliters of each fraction was added to scintillation fluid and counted. Most protein-associated counts were found in fractions 44–47. FIG. 5A shows electrophoresis of fractions 40 (lane 2), 44 (lane 3), 46 (lane 4) and 47 (lane 5) from one chromatography run through a 14% Tris-glycine polyacrylamide-SDS gel, followed by coomassie staining. This gel was then processed with Entensigy (NEN) and exposed to film for 18 hours, as shown in FIG. 5B. Each fraction contained several proteins as shown in FIG. 5A, but only 4 bands were labeled, the most prominent being 26 kd (seen in lanes 3, 4 and 5), and denoted herein as PfSP26. A faint band of 24 kd, denoted herein as PfSP24, was also noticed in lane 5. A band of 19 kD, denoted herein as PfSP19, was labeled in lane 4 that was associated with a very faintly staining protein band. Some labeled proteins were seen at the dye front of lanes 4 and 5, indicating a molecular weight less than 6 kd, denoted herein as PfSP6, and could be degradation products.

Fraction 44 (analogous to lane 3) from a second C4 chromatography separation experiment was electrophoresed, blotted onto PVDF, stained with Coomassie R-250 and destained via standard procedures. The 26 kd band, corresponding to PfSP26, was excised and subjected to N-terminal amino acid sequencing using techniques known to those skilled in the art. A partial N-terminal amino acid sequence of about 32 amino acids was deduced and is represented herein as SEQ ID NO:1:

Ile Ile Gly Glu Gly Val Ala Gly Glu Gly Ser Ala Pro Tyr Gln Val Ser Leu Arg Thr Lys Glu Gly Asn His Phe Ser Gly Gly Ser Ile Leu

It should be noted that since amino acid sequencing technology is not entirely error-free, SEQ ID NO:1 represents, at best, an apparent partial N-terminal amino acid sequence of PfSP26. This caution is particularly relevant in light of the sequencing of this protein having been done at a low picomolar concentration.

A homology search of the non-redundant protein sequence database was performed through the National Center for Biotechnology Information using the BLAST network. This database includes +SwissProt+PIR+SPUpdate+GenPept+GPUpdate.ole level. Results of the search indicate that the N-terminus of PfSP26 shares significant amino sequence homology with a number of serine proteases, including a variety of trypsins, chymotrypsins and plasmins. The 32-amino acid N-terminal amino acid sequence of PfSP26 shared the highest degree of homology (about 53% identity) with *Drosophila melanogaster* trypsin-theta.

Example 8

This example describes the cloning of certain flea protease nucleic acid molecules of the present invention. This example also describes the production of certain recombinant molecules, recombinant cells and flea protease proteins of the present invention.

Several flea serine protease nucleic acid molecules, ranging in size from about 250 to about 500 nucleotides, and representing one or more partial flea serine protease genes, were PCR amplified from a fed flea midgut cDNA library that was prepared from RNA isolated from fed flea midguts using standard protocols as described in Sambrook et al., ibid. Several pairs of primers were used in PCR amplification reactions that represented degenerate oligonucleotides designed from published sequences of serine protease genes isolated from biting insects (e.g., mosquitos and black flies). Each primer pair was designed so that a properly amplified fragment of a flea serine protease gene would include a domain corresponding to the most conserved domain of trypsin protease genes (thought to be the active site) given that such a domain is contained in flea serine protease gene(s).

The amplified PCR fragments were of predicted size, ranging from about 250 nucleotides to about 500 nucleotides, depending on which primer pairs were used. PCR fragments that hybridized to a probe designed from the domain most conserved among all known trypsin genes were gel purified and cloned, for example, into the pCRII cloning vector (available from Invitrogen, San Diego, Calif.), following manufacturer's instructions. Nucleic acid sequences of the fragments are being determined using standard techniques.

The amplified PCR fragments are also being used as probes to identify full-length flea protease genes in unfed and fed flea midgut cDNA libraries and in flea salivary gland cDNA libraries, as well as in flea genomic DNA libraries, using standard procedures.

Recombinant molecules and recombinant cells including the amplified PCR fragments as well as full-length flea protease genes are being produced using standard procedures. Culturing of such recombinant cells leads to the production of flea protease proteins of the present invention.

Example 9

This Example describes the testing of a flea protease protein as a flea protease vaccine of the present invention, that is for the ability of such a protein, upon administration to an animal, to elicit the production of antibodies that reduce flea protease activity and, as such, reduce flea viability and/or fecundity. This Example also demonstrates the use of such a flea protease protein as a vaccine on a dog subsequently infested with fleas.

A flea protease protein produced as described in Example 7 is administered to rabbits according to a standard immunization protocol known to those skilled in the art, including appropriate booster shots. Such a protein is also administered to guinea pigs and to dogs following a similar protocol.

Sera is collected from the treated rabbits and is verified to contain anti-flea protease antibodies. Such sera is then fed to fleas in a feeding system as reported by Wade et al. ibid. Fleas feeding on such a sera show reduced viability compared to fleas feeding on sera collected from rabbits not administered the flea protease protein. Sera from treated guinea pigs and dogs are verified in a similar manner.

Dogs treated with a flea protease protein are then infested with fleas as are dogs not treated with a flea protease protein. Dogs treated with a flea protease protein show a significant reduction in flea burden compared to untreated dogs.

SEQUENCE LISTING

The following Sequence Listing is submitted pursuant to 37 CFR §1.821. A copy in computer readable form is also submitted herewith.

Applicants assert pursuant to 37 CFR §1.821(f) that the content of the paper and computer readable copies of SEQ ID NO:1 submitted herewith are the same.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Ile  Ile  Gly  Glu  Gly  Val  Ala  Gly  Glu  Gly  Ser  Ala  Pro  Tyr  Gln  Val
 1              5                         10                           15

Ser  Leu  Arg  Thr  Lys  Glu  Gly  Asn  His  Phe  Ser  Gly  Gly  Ser  Ile  Leu
           20                       25                           30
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to treat a host animal for flea infestation comprising administering to said animal, a composition comprising a compound that reduces protease activity of fleas feeding from said treated animal, thereby reducing the fecundity of female fleas that feed from said animal.

2. The method of claim 1, wherein said protease is selected from the group consisting of an aminopeptidase, a carboxypeptidase, an endopeptidase, and a mixture thereof.

3. The method of claim 1, wherein said protease is selected from the group consisting of a serine protease, a metalloprotease, an aspartic acid protease and a cysteine protease.

4. The method of claim 1, wherein said protease is selected from the group consisting of a serine protease, a metalloprotease, and a mixture thereof.

5. The method of claim 1, wherein said protease comprises a serine protease.

6. The method of claim 1, wherein said protease comprises an aminopeptidase.

7. The method of claim 1, wherein said protease is selected from the group consisting of a trypsin-like protease, a chymotrypsin-like protease, an aminopeptidase, and a mixture thereof.

8. The method of claim 1, wherein said compound comprises a flea protease inhibitor selected from the group consisting of a serine protease inhibitor, a metalloprotease inhibitor, an aspartic acid protease inhibitor, a cysteine protease inhibitor, an aminopeptidase inhibitor and a mixture thereof.

9. The method of claim 1, wherein said compound comprises a flea protease inhibitor selected from the group consisting of a serine protease inhibitor, a metalloprotease inhibitor, an aminopeptidase inhibitor, and a mixture thereof.

10. The method of claim 1, wherein said compound comprises a flea serine protease inhibitor.

11. The method of claim 1, wherein said composition further comprises a component selected from the group consisting of a pharmaceutically acceptable excipient, an adjuvant, a carrier, and a mixture thereof.

12. The method of claim 1, wherein said step of treating said animal reduces the fecundity of female fleas that feed from said treated animal.

13. The method of claim 1, wherein said composition is administered by at least one route selected from the group consisting of oral, nasal, topical, transdermal, rectal, and parenteral routes.

14. The method of claim 1, wherein said animal is selected from the group consisting of mammals and birds.

15. The method of claim 1, wherein said animal is selected from the group consisting of cats and dogs.

16. The method of claim 1, wherein said fleas are of a genus selected from the group consisting of Ctenocephalides, Cyopsyllus, Diamanus, Echidnophaga, Nosopsyllus, Pulex, Tunga, and Xenopsylla.

17. The method of claim 1, wherein said fleas are of a species selected from the group consisting of Ctenocephalides felis, Ctenocephalides canis, Pulex irritans and Pulex simulans.

18. The method of claim 1, wherein said composition comprises a controlled release formulation.

19. The method of claim 18, wherein said controlled release formulation comprises a biocompatible polymer.

20. The method of claim 18, wherein said controlled release formulation comprises a liquid that upon administration to said animal forms a solid or a gel in situ.

21. The method of claim 18, wherein said controlled release formulation is biodegradable.

22. The method of claim 18, wherein said controlled release formulation is capable of effecting said treatment for at least about 1 month after administration of said controlled release formulation to said animal.

23. A method to treat an animal for flea infestation comprising administering to said animal a controlled release formulation comprising a composition capable of reducing flea protease activity of fleas feeding from said treated animal, thereby reducing the fecundity of female fleas that feed from said animal.

* * * * *